United States Patent
Dai et al.

(10) Patent No.: US 6,335,169 B1
(45) Date of Patent: Jan. 1, 2002

(54) NUCLEIC ACIDS ENCODING HBUB1, A CELL CYCLE CHECKPOINT GENE

(75) Inventors: Wei Dai; Bin Ouyang; Huiqi Pan; Zhengdao Lan, all of Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/448,806

(22) Filed: Nov. 24, 1999

Related U.S. Application Data

(60) Provisional application No. 60/110,218, filed on Nov. 30, 1998.

(51) Int. Cl.$^7$ ............................... C12Q 1/68; C12N 15/54

(52) U.S. Cl. ..................... 435/6; 435/320.1; 435/252.3; 435/325; 435/194; 536/23.2

(58) Field of Search ............................... 435/6, 15, 320.1, 435/252.3, 325, 194; 536/23.2

(56) References Cited

FOREIGN PATENT DOCUMENTS

WO           98/56910     * 12/1998

OTHER PUBLICATIONS

Pangilinan, F., et al. (1997) Genomics 46, 379–388.*
Accession No. AF043294 (1998).*
Accession No. AF046078 (1997).*
Ted Weinert, A DNA Damage Checkpoint Meets the Cell Cycle Engine, Science, vol. 227, Sep. 5, 1997, pp. 1450–1451.
Kim Nasmyth, Viewpoint: Putting the Cell Cycle in Order, Science, vol. 274, Dec. 6, 1996, pp. 1643–1645.
Jonathan Pines, The cell cycle kinases, Seminars in Cancer Biology, vol. 5, 1994, pp. 305–313.
Stephen J. Elledge, Cell Cycle Checkpoints: Preventing an Identity Crisis, Science, vol. 274, Dec. 6, 1996, pp. 1664–1671.
Amanda G. Paulovich, et al., When Checkpoints Fail, Cell, vol. 88, Feb. 7, 1997, pp. 315–321.
M. Andrew Hoyt, et al., S. cerevisiae Genes Required for Cell Cycle Arrest in Response to Loss of Microtubule Function, Cell, vol. 66, Aug. 9, 1991, pp. 507–517.
Rong Li, et al., Feedback Control of Mitosis in Budding Yeast, Cell, vol. 66, Aug. 9, 1991, pp. 519–531.
Kevin G. Hardwick, The spindle checkpoint, Trends In Genetics, vol. 14 No. 1, Jan., 1998, pp. 1–4.
B. Tibor Roberts, et al., The Saccharomyces cerevisiae Checkpoint Gene BUB1 Encodes a Novel Protein Kinase, Molecular and Cellular Biology, Vo. 14, Dec., 1994, pp. 8282–8291.
Katie A. Farr, et al., Bub1p Kinase Activates the Saccharomyces cerevisiae Spindle Assembly Checkpoint, Molecular and Cellular Biology, vol. 18, May 1998, pp. 2738–2747.

C. Frankhauser, et al., The S.pombe cdc 16 Gene is Required both for Maintenance of p34cdc2 Kinase Activity & Regulation of Septurn Formation: A Link Between Mitosis and Cytokinesis?, Embo J., vol. 12, 1993, pp. 2697–2704.
Kevin G. Hardwick, et al., Mad1p, a Phosphoprotein Component of the Spindle Assembly Checkpoint in Budding Yeast, The Journal of Cell Biology, vol. 131, No. 3, Nov. 1995, pp. 709–720.
Yong Li, et al., Identification of a Human Mitotic Checkpoint Gene: hsMAD2, Science, vol. 274, Oct. 11, 1996, pp. 246–248.
Rey–Huei Chen, et al., Association of Spindle Assembly Checkpoint Component XMAD2 with Unattached Kinetochores, Science, vol. 274, Oct. 11, 1996, pp. 242–245.
Stephen S. Taylor, et al., Kinetochore Localization of Murine Bub1 Is Required for Normal Mitotic Timing and Checkpoint Response to Spindle Damage, Cell, vol. 89, May 30, 1997, pp. 727–735.
Daniel P. Cahill, et al., Mutations of Mitotic Checkpoint Genes in Human Cancers, Nature, vol. 392, Mar. 19, 1998, pp. 300–303.

(List continued on next page.)

Primary Examiner—Charles L. Patterson, Jr.
(74) Attorney, Agent, or Firm—Frost Brown Todd LLC

(57) ABSTRACT

Eukaryotic cells have evolved a mechanism that delays the onset of anaphase until chromosomes are properly positioned on the spindle. To understand the molecular basis of such surveillance mechanism in human cells, we have cloned a full-length cDNA encoding a putative mitotic checkpoint kinase termed hBub1. Sequence comparison reveals that hBub1 is a structurally conserved protein, sharing 23% amino acid residue identity with BUB1 of budding yeast. In addition, the N-terminal portion (161 amino acids) of hBub1 shows a significant homology to yeast MAD3, a protein also known to be involved in the mitotic checkpoint response pathway. Northern blot analyses show that hBub1 mRNA level is abundantly expressed in tissues or cells with a high mitotic index. When Dami cells undergoes terminal differentiation following treatment with phorbol ester, hBub1 expression in this cell line is rapidly downregulated. The hBub1 protein level is low in G1 and remains relatively constant in S, G2 and M phases. Immunofluorescence analysis shows that hBub1 protein co-localizes with a centromere-kinetochore antigen CREST in interphase, mitotic prophase and nocodazole-treated cells. Antibody electroporation experiments show that hBub1 is an important component of the spindle checkpoint pathway. Furthermore, fluorescence in situ hybridization analysis maps the hBub1 gene to chromosome 2q12–13. Our studies suggest that hBub1 expression is restricted to proliferating cells and appears to be involved in regulating cell-cycle progression. The molecular cloning of hBub1 cDNA will facilitate the study of its role in spindle checkpoint control as well as its potential role in certain genetic disorders.

31 Claims, 11 Drawing Sheets

OTHER PUBLICATIONS

N.S. Duesbery, et al., CENP–E is an Essential Kinetochore Motor in Maturing Oochtes and is Masked During Mos–dependent, Cell Cycle Arrest at Metaphase II., *Proc. Natl. Acad. Sci. USA*, vol. 94, 1997, pp. 9165–9170.

Henry H.Q. Heng, et al., High–resolution Mapping of Mammalian Genes by in situ Hybridization to Free Chromatin, *Proc. Natl. Acad. Sci. USA*, vol. 89, Oct. 1992, pp. 9509–9513.*

Henry H.Q. Heng, et al., Modes of DAPI banding and simultaneous in situ hybridization, *Chromosoma*, vol. 102, 1993, pp. 325–332.*

Heiko Hermeking, et al., 14–3–3α Is a p53–Regulated Inhibitor of G2/M Progression, *Molecular Cell*, vol. 1, Dec. 1997, pp. 3–11.*

Marilyn Kozak, Compilation and Analysis of Sequences Upstream from the Transitionally Start Site in Eukaryotic mRNAs, *Nucleic Acids Research*, vol. 12, No. 2, 1984, pp. 857–872.*

Steven K. Hanks, et al., The Protein Kinase Family: Conversed Features and Deduced Phylogeny of the Catalytic Domains, *Science*, vol. 241, pp. 42–52. (1988).*

Yoko Sekine, et al., A Novel Microtubule–based Motor Protein (KIF4) for Organelle Transports, Whose Expression Is Regulated Developmentally, *The Journal of Cell Biology*, vol. 127, No. 1, Oct. 1994, pp. 187–201.*

Sheryl M Greenberg, et al., Characterization of a New Megakaryocytic Cell Line: The Dami Cell, *Blood*, vol. 72, No. 6, Dec. 1988, pp. 1968–1977.*

Bin Ouyang, et al., Human Prk Is a Conserved Protein Serine/Threonine Kinase Involved in Regulating M. Phase Functions, *The Journal of Biological Chemistry*, vol. 272, No. 45, Nov. 7, 1997, pp. 28646–28651.*

Bo Li, et al., prk, a Cytokine–inducible Human Protein Serine/Threonine Kinase Whose Expression Appears to be Down–regulated in Lung Carcinomas, *The Journal of Biological Chemistry*, vol. 271, No. 32, Aug. 9, 1996, pp. 19402–19408.*

Charles J. Sherr, Cancer Cell Cycles, *Science*, vol. 274, Dec. 6, 1996, pp. 1672–1677.*

Yang Xu, et al., Targeted disruption of ATM leads to growth retardation, chromosomal fragmentation during meiosis, immune defects, and thymic lymphoma, *Genes and Development*, vol. 10, 1996, pp. 2411–2422.*

Yolanda Sanchez, et al., Conservation of the Chk1 Checkpoint Pathway in Mammals: Linkage of DNA Damage to Cdk Regulation Through Cdc25, *Science*, vol. 277, Sep. 5, 1997, pp. 1497–1501.*

Bin Ouyang, et al., Human Bub1: A Putative Spindle Checkpoint Kinase Closely Linked to Cell Proliferation, *Cell Growth & Differentiation*, vol. 9, Oct. 1998, pp. 877–885.*

Wenqing Li, et al., BUBR1 Phosphorylation Is Regulated during Mitotic Checkpoint Activation, *Cell Growth & Differentiation*, vol. 10, Nov. 1999, pp. 769–775.*

* cited by examiner-

```
GGTTTGCCGCTGCCGCCCAGCGTCTTTTGGCCATGGACACCCCGGAAAATGTCCTTCAGA    60
                                  M  D  T  P  E  N  V  L  Q

TGCTTGAAGCCCACATGCAAGAGTACAAGGGCAATGACCTTCTTGGTGAATGGGAAGAT    120
 M  L  E  A  H  M  Q  E  Y  K  G  N  D  L  L  G  E  W  E  R

ACATACAGTGGGTAGAAGAGAATTTTCCTGAGAATAAAGAATACTTGATAACTTTACTAG    180
 Y  I  Q  W  V  E  E  N  F  P  E  N  K  E  Y  L  I  T  L  L

AACATTTAATGAAGGAATTTTTAGATAAGAAGAAATACCACAATGACCCAAGATTCATCA    240
 E  H  L  M  K  E  F  L  D  K  K  K  Y  H  N  D  P  R  F  I

GTTATTGTTTAAAATTTGCTGAGTACAACAGTGACCTCCATCAATTTTTTGAGTTTCTGT    300
 S  Y  C  L  K  F  A  E  Y  N  S  D  L  H  Q  F  F  E  F  L

ACAACCATGGGATTGGAACCCTGTCATCCCCTCTGTACATTGCCTGGGCGGGGCATCTGG    360
 Y  N  H  G  I  G  T  L  S  S  P  L  Y  I  A  W  A  G  H  L

AAGCCCAAGGAGAGCTGCAGCATGCCAGTGCTGTCCTTCAGAGAGGAATTCAAAACCAGG    420
 E  A  Q  G  E  L  Q  H  A  S  A  V  L  Q  R  G  I  Q  N  Q

CTGAACCCAGAGAGTTCCTGCAACAACAATACAGGTTATTTCAGACACGCCTCACTGAAA    480
 A  E  P  R  E  F  L  Q  Q  Q  Y  R  L  F  Q  T  R  L  T  E

CCCATTTGCCAGCTCAAGCTAGAACCTCAGAACCTCTGCATAATGTTCAGGTTTTAAATC    540
 T  H  L  P  A  Q  A  R  T  S  E  P  L  H  N  V  Q  V  L  N

AAATGATAACATCAAAATCAAATCCAGGAAATAACATGGCCTGCATTTCTAAGAATCAGG    600
 Q  M  I  T  S  K  S  N  P  G  N  N  M  A  C  I  S  K  N  Q

GTTCAGAGCTTTCTGGAGTGATATCTTCAGCTTGTGATAAAGAGTCAAATATGGAACGAA    660
 G  S  E  L  S  G  V  I  S  S  A  C  D  K  E  S  N  M  E  R

GAGTGATCACGATTTCTAAATCAGAATATTCTGTGCACTCATCTTTGGCATCCAAAGTTG    720
 R  V  I  T  I  S  K  S  E  Y  S  V  H  S  S  L  A  S  K  V

ATGTTGAGCAGGTTGTTATGTATTGCAAGGAGAAGCTTATTCGTGGGGAATCAGAATTTT    780
 D  V  E  Q  V  V  M  Y  C  K  E  K  L  I  R  G  E  S  E  F

CCTTTGAAGAATTGAGAGCCCAGAAATACAATCAACGGAGAAAGCATGAGCAATGGGTAA    840
 S  F  E  E  L  R  A  Q  K  Y  N  Q  R  R  K  H  E  Q  W  V

ATGTAGACAGACATTATATGAAAAGGAAAGAAGCAAATGCTTTTGAAGAACAGCTATTAA    900
 N  V  D  R  H  Y  M  K  R  K  E  A  N  A  F  E  E  Q  L  L

AACAGAAAATGGATGAACTTCATAAGAAGTTGCATCAGGTGGTGGAGACATCCCATGAGG    960
 K  Q  K  M  D  E  L  H  K  K  L  H  Q  V  V  E  T  S  H  E

ATCTGCCCGCTTCCCAGGAAAGGTCCGAGGTTAATCCAGCACGTATGGGGCCAAGTGTAG    1020
 D  L  P  A  S  Q  E  R  S  E  V  N  P  A  R  M  G  P  S  V

GCTCCCAGCAGGAACTGAGAGCGCCATGTCTTCCAGTAACCTATCAGCGGACACCAGTGA    1080
 G  S  Q  Q  E  L  R  A  P  C  L  P  V  T  Y  Q  R  T  P  V
```

FIGURE 1 - A1

```
ACATGGAAAAGAACCCAAGAGAGGCACCTCCTGTTGTTCCTCCTTTGGCAAATGCTATTT   1140
 N  M  E  K  N  P  R  E  A  P  P  V  V  P  P  L  A  N  A  I

CTGCAGCTTTGGTGTCCCCAGCCACCAGCCAGAGCACTGCTCCTCCTGTTCCTTTGAAAG   1200
 S  A  A  L  V  S  P  A  T  S  Q  S  T  A  P  P  V  P  L  K

CCCAGACAGTAACAGACTCCATGTATGCAGTGGCCAGCAAAGATGCTGGATGTGTGAATA   1260
 A  Q  T  V  T  D  S  M  Y  A  V  A  S  K  D  A  G  C  V  N

AGAGTACTCATGAATTCAAGCCACAGAGTGGAGCAGAGATCAAAGAAGGGTGTGAAACAC   1320
 K  S  T  H  E  F  K  P  Q  S  G  A  E  I  K  E  G  C  E  T

ATAAGGTTGCCAACACAAGTTCTTTTCACACAACTCCAAACACATCACTGGGAATGGTTC   1380
 H  K  V  A  N  T  S  S  F  H  T  T  P  N  T  S  L  G  M  V

AGTCAACGCCATCCAAAGTGCAGCCATCACCCACCGTGCACACAAAAGAAGCATTAGGTT   1440
 Q  S  T  P  S  K  V  Q  P  S  P  T  V  H  T  K  E  A  L  G

TCATCATGAATATGTTTCAGGCTCCTACACTTCCTGATATTTCTGATGACAAAGATGAAT   1500
 F  I  M  N  M  F  Q  A  P  T  L  P  D  I  S  D  D  K  D  E

GGCAATCTCTAGATCAAAATGAAGATGCATTTGAAGCCCAGTTTCAAAAAAATGTAAGGT   1560
 W  Q  S  L  D  Q  N  E  D  A  F  E  A  Q  F  Q  K  N  V  R

CATCTGGGGCTTGGGGAGTCAATAAGATCATCTCTTCTTTGTCATCTGCTTTTCATGTGT   1620
 S  S  G  A  W  G  V  N  K  I  I  S  S  L  S  S  A  F  H  V

TTGAAGATGGAAACAAAGAAAATTATGGATTACCACAGCCTAAAAATAAACCCACAGGAG   1680
 F  E  D  G  N  K  E  N  Y  G  L  P  Q  P  K  N  K  P  T  G

CCAGGACCTTTGGAGAACGCTCTGTCAGCAGACTTCCTTCAAAACCAAAGGAGGAAGTGC   1740
 A  R  T  F  G  E  R  S  V  S  R  L  P  S  K  P  K  E  E  V

CTCATGCTGAAGAGTTTTTGGATGACTCAACTGTATGGGGTATTCGCTGCAACAAAACCC   1800
 P  H  A  E  E  F  L  D  D  S  T  V  W  G  I  R  C  N  K  T

TGGCACCCAGTCCTAAGAGCCCAGGAGACTTCACATCTGCTGCACAACTTGCGTCTACAC   1860
 L  A  P  S  P  K  S  P  G  D  F  T  S  A  A  Q  L  A  S  T

CATTCCACAAGCTTCCAGTGGAGTCAGTGCACATTTTAGAAGATAAAGAAAATGTGGTAG   1920
 P  F  H  K  L  P  V  E  S  V  H  I  L  E  D  K  E  N  V  V

CAAAACAGTGTACCCAGGCGACTTTGGATTCTTGTGAGGAAAACATGGTGGTGCTTTCAA   1980
 A  K  Q  C  T  Q  A  T  L  D  S  C  E  E  N  M  V  V  L  S

GGGATGGAAAATTCAGTCCAATTCAAGAGAAAAGCCCAAAACAGGCCTTGTCGTCTCACA   2040
 R  D  G  K  F  S  P  I  Q  E  K  S  P  K  Q  A  L  S  S  H

TGTATTCAGCATCCTTACTTCGTCTGAGCCAGCCTGCTGCAGGTGGGGTACTTACCTGTG   2100
 M  Y  S  A  S  L  L  R  L  S  Q  P  A  A  G  G  V  L  T  C

AGGCAGAGTTGGGCGTTGAGGCTTGCAGACTCACAGACACTGACGCTGCCATTGCAGAAG   2160
 E  A  E  L  G  V  E  A  C  R  L  T  D  T  D  A  A  I  A  E

ATCCACCAGATGCTATTGCTGGGCTCCAAGCAGAATGGATGCAGATGAGTTCACTTGGGA   2220
 D  P  P  D  A  I  A  G  L  Q  A  E  W  M  Q  M  S  S  L  G
```

FIGURE 1 - A2

```
CTGTTGATGCTCCAAACTTCATTGTTGGGAACCCATGGGATGATAAGCTGATTTTCAAAC    2280
 T  V  D  A  P  N  F  I  V  G  N  P  W  D  D  K  L  I  F  K

TTTTATCTGGGCTTTCTAAACCAGTGAGTTCCTATCCAAATACTTTTGAATGGCAATGTA    2340
 L  L  S  G  L  S  K  P  V  S  S  Y  P  N  T  F  E  W  Q  C

AACTTCCAGCCATCAAGCCCAAGACTGAATTTCAATTGGGTTCTAAGCTGGTCTATGTCC    2400
 K  L  P  A  I  K  P  K  T  E  F  Q  L  G  S  K  L  V  Y  V

ATCACCTTCTTGGAGAAGGAGCCTTTGCCCAGGTGTACGAAGCTACCCAGGGAGATCTGA    2460
 H  H  L  L  G  E  G  A  F  A  Q  V  Y  E  A  T  Q  G  D  L

ATGATGCTAAAAATAAACAGAAATTTGTTTTAAAGGTCCAAAAGCCTGCCAACCCCTGGG    2520
 N  D  A  K  N  K  Q  K  F  V  L  K  V  Q  K  P  A  N  P  W

AATTCTACATTGGGACCCAGTTGATGGAAAGACTAAAGCCATCTATGCAGCACATGTTTA    2580
 E  F  Y  I  G  T  Q  L  M  E  R  L  K  P  S  M  Q  H  M  F

TGAAGTTCTATTCTGCCCACTTATTCCAGAATGGCAGTGTATTAGTAGGAGAGCTGTACA    2640
 M  K  F  Y  S  A  H  L  F  Q  N  G  S  V  L  V  G  E  L  Y

GCTATGGAACATTATTAAATGCCATTAACCTTTATAAAAATACCCCTGAAAAAGTGATGC    2700
 S  Y  G  T  L  L  N  A  I  N  L  Y  K  N  T  P  E  K  V  M

CTCAAGGTCTTGTCATCTCTTTCGCTATGAGAATGCTTTACATGATTGAGCAAGTGCATG    2760
 P  Q  G  L  V  I  S  F  A  M  R  M  L  Y  M  I  E  Q  V  H

ACTGTGAAATCATTCATGGAGACATTAAGCCAGATAACTTCATACTTGGAAACGGATTTT    2820
 D  C  E  I  I  H  G  D  I  K  P  D  N  F  I  L  G  N  F

TGGAACAGGATGATGAAGATGATTTATCTGCTGGCTTGGCACTGATTGACCTGGGTCAGA    2880
 L  E  Q  D  D  E  D  D  L  S  A  G  L  A  L  I  D  L  G  Q

GTATAGATATGAAACTTTTTCCAAAAGGAACTATATTCACAGCAAAGTGTGAAACATCTG    2940
 S  I  D  M  K  L  F  P  K  G  T  I  F  T  A  K  C  E  T  S

GTTTTCAGTGTGTTGAGATGCTCAGCAACAAACCATGGAACTACCAGATCGATTACTTTG    3000
 G  F  Q  C  V  E  M  L  S  N  K  P  W  N  Y  Q  I  D  Y  F

GGGTTGCTGCAACAGTATATTGCATGCTCTTTGGCACTTACATGAAAGTGAAAAATGAAG    3060
 G  V  A  A  T  V  Y  C  M  L  F  G  T  Y  M  K  V  K  N  E

GAGGAGAGTGTAAGCCTGAAGGTCTTTTTAGAAGGCTTCCTCATTTGGATATGTGGAATG    3120
 G  G  E  C  K  P  E  G  L  F  R  R  L  P  H  L  D  M  W  N

AATTTTTTCATGTTATGTTGAATATTCCAGATTGTCATCATCTTCCATCTTTGGATTTGT    3180
 E  F  F  H  V  M  L  N  I  P  D  C  H  H  L  P  S  L  D  L

TAAGGCAAAAGCTGAAGAAAGTATTTCAACAACACTATACTAACAAGATTAGGGCCCTAC    3240
 L  R  Q  K  L  K  K  V  F  Q  Q  H  Y  T  N  K  I  R  A  L

GTAATAGGCTAATTGTACTGCTCTTAGAATGTAAGCGTTCACGAAAATAAAATTTGGATA    3300
 R  N  R  L  I  V  L  L  E  C  K  R  S  R  K  *

TAGACAGTCCTTAAAAAAAAAAAAAAAAAAAA                                3332
```

FIGURE 1 - A3

NUCLEIC ACIDS ENCODING HBUB1, A CELL CYCLE CHECKPOINT GENE

This is a non-provisional application based upon an earlier filed provisional application, Serial No. 60/110,218 filed, Nov. 30, 1998.

This invention was made in part with government support under grant RO1CA74299 awarded by the National Institutes of Health. The government has certain rights in the invention.

FIELD OF THE INVENTION

This invention relates generally to genetic engineering involving recombinant DNA technology, and particularly to the identification of nucleic acid molecules capable of hybridizing under stringent conditions to the nucleotide sequence of the hBub1 cDNAs shown in SEQ ID NO: 1 or GenBank Accession NO: AF043294.

BACKGROUND OF THE INVENTION

Eukaryotic cells respond to internal demands or sense the external environment by remaining quiescent, staying in the cell cycle, or activating cell death programs. The coordination of such a complex process necessarily entails very sensitive and sophisticated regulation. Increasing evidence indicates that protein kinases and phosphatases are central to the regulation of these events (1–3).

Extensive research in the past has led to the identification of cellular mechanisms (commonly referred to as checkpoints) that monitor the readiness of a cell to enter the next stage of the cell cycle (4,5). There are two major checkpoints controlling the G2M transition and M-phase progression. In yeast, cdc2/CDC28 kinase is pivotal in the G2/M transition (3) while the spindle checkpoint kinase BUB1 is thought to be involved in regulating mitotic progression (6,7). Genetic analyses have identified six distinct yeast genes (BUB1, 2, and 3 and MAD1, 2, and 3) that are important in regulating the spindle checkpoint (6–8). BUB1 encodes a protein serine/threonine kinase and is itself phosphorylated when the cell enters mitosis (9). A recent study shows that Bub1p activates the spindle checkpoint in the budding yeast (10). BUB2 is structurally related to the fission yeast cdc16 gene product, which plays an essential part in cytokinesis (11). BUB3, unrelated to any other known proteins, appears to be a substrate of BUB1 (9). MAD1 protein is hyperphosphorylated when wild type yeast cells are arrested in mitosis upon disruption of microtubules (12). MAD2 is required for MAD1 hyperphosporylation in yeast (7,12), and yeast MAD3 is a 60-kDa protein whose biochemical function remains unknown (7).

Until recently, little was known regarding the molecular components in spindle checkpoint regulation in high eukaryotes. It has been shown that human Mad2, structurally and functionally conserved (13), is localized at the kinetochore after chromosome condensation but not after metaphase (13). XMAD2 from Xenopus is co-localized with unattached kinetochores in prometaphase but disappeared from the apparatus in metaphase (14). It has also been demonstrated that human Mad2 expression is down-regulated in a human breast cancer cell line that is sensitive to taxol and nocodazole (13). Murine Bub1 (mnBub1) has recently been cloned and characterized (15). The mBub1 protein also localizes to the kinetochore during early mitosis (15). When mBub1 function is compromised, cells are unable to appropriately initiate programmed cell death when an apoptotic signal is present (15). The hBub1 gene has recently been implicated in the development of certain colorectal cancers (16).

BRIEF SUMMARY OF THE INVENTION

The present invention relates generally to the field of human genetics. Specifically, the present invention relates to methods and materials used to isolate and detect a human gene (hBub1), some alleles of which cause susceptibility to cancer. More specifically, the present invention relates to germline mutations in the hBub1 gene and their use in the diagnosis of predisposition to cancer. The invention further relates to somatic mutations in the hBub1 gene in human cancer and their use in the diagnosis and prognosis of human cancer. Additionally, the invention relates to somatic mutations in the hBub1 gene in other human cancers and their use in the diagnosis and prognosis of human cancers. The invention also relates to the therapy of human cancers which have a mutation in the hBub1 gene, including gene therapy, protein replacement therapy and protein mimetics. The invention further relates to the screening of drugs for cancer therapy. Finally, the invention relates to the screening of the hBub1 gene for mutations, which are useful for diagnosing the predisposition to cancer.

The present invention provides an isolated polynucleotide comprising all, or a portion of the hBub1 locus or of a mutated hBub1 locus, preferably at least eight bases and not more than about 100 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the hBub1 locus or its expression product in an analyte. Such methods may further comprise the step of amplifying the portion of the hBub1 locus, and may further include a step of providing a set of polynucleotides that are primers for amplification of said portion of the hBub1 locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the hBub1 locus.

The present invention also provides kits for detecting in an analyte a polynucleotide comprising a portion of the hBub1 locus, the kits comprising a polynucleotide complementary to the portion of the hBub1 locus packaged in a suitable container, and instructions for its use.

The present invention further provides methods of preparing a polynucleotide comprising polymerizing nucleotides to yield a sequence comprised of at least eight consecutive nucleotides of the hBub1 locus; and methods of preparing a polypeptide comprising polymerizing amino acids to yield a sequence comprising at least five amino acids encoded within the hBub1 locus.

The present invention further provides methods of screening the hBub1 gene to identify mutations. Such methods may further comprise the step of amplifying a portion of the hBub1 locus, and may further include a step of providing a set of polynucleotides that are primers for amplification of said portion of the hBub1 locus. The method is useful for identifying mutations for use in either diagnosis of the predisposition to cancer or the diagnosis or prognosis of cancer.

The present invention further provides methods of screening suspected hBub1 mutant alleles to identify mutations in the hBub1 gene.

In addition, the present invention provides methods of screening drugs for cancer therapy to identify suitable drugs for restoring hBub1 gene product function.

Finally, the present invention provides the means necessary for production of gene-based therapies directed at cancer cells. These therapeutic agents may take the form of polynucleotides comprising all or a portion of the hBub1 locus placed in appropriate vectors or delivered to target cells in more direct ways such that the function of the hBub1 protein is reconstituted. Therapeutic agents may also take the form of polypeptides based on either a portion of, or the entire protein sequence of hBub1. These may functionally replace the activity of hBub1 in vivo.

BRIEF DESCRIPTION OF THE FIGURES

FIG. 1. Nucleotide sequence and deduced amino acid sequence of hBub1. (SEQ ID NO: 1). Amino acids are numbered from the initiating methionine. (SEQ ID NO. 2). The putative nuclear targeting signal is underlined. The amino acids thought to be involved in ATP binding are double-underlined. The sequence used for production of anti-hBub1 antibody is highlighted with a broken underline.

DETAILED DESCRIPTION OF THE INVENTION

Figure 2:
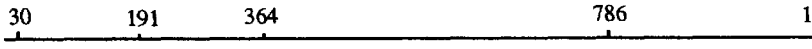
FIGS. 2A, 2B and 2B Sequence identity and similarity between the deduced hBub1 (SEQ ID NO: 3, SEQ ID NO. 5, SEQ ID NO. 7 and SEQ ID NO. 9) and MAD3 (SEQ ID NO: 4 and SEQ ID NO. 6) of S. cerevisiae (A) or murine kinesin-like protein muKIF4 (SEQ ID NO: 8 and SEQ ID NO. 10) (B). A & B. Double vertical dots indicate the amino acid residue identity and the single dot indicates residue similarity. C. Schematic representation of hBub1 protein domain structure.

Prior to setting forth the invention, it may be helpful to set forth definitions of certain terms to be used within the disclosure.

"Antibody" refers to a molecule that is a member of a family of glycosylated proteins called immunoglobulins that can specifically combine with an antigen. Such an antibody combines with its antigen by a specific immunologic binding interaction between the antigenic determinant of the antigen and the antibody-combining site of the antibody.

"Antigen" has been used historically to designate an entity that is bound by an antibody, and also to designate the entity that induces the production of the antibody. More current usage limits the meaning of antigen to that entity bound by an antibody, whereas the word "immunogen" is used for the entity that induces antibody production. Where an entity discussed herein is both immunogenic and antigenic, it will generally be termed an antigen.

"Biological activity" refers to a function or set of activities performed by a molecule in a biological context (i.e., in an organism or an in vitro facsimile thereof). Biological activities may include the induction of extracellular matrix secretion from responsive cell lines, the induction of hormone secretion, the induction of chemotaxis, the induction of mitogenesis, the induction of differentiation, or the inhibition of cell division of responsive cells. A recombinant protein or peptide is considered to be biologically active if it exhibits one or more biological activities of its native counterpart.

Biological activity of a paratopic molecule containing an antibody-combining site is evidenced by the immunologic reaction of the paratope (antibody combining site) with its epitope (antigenic determinant) upon their admixture in an aqueous medium to form an immunoreactant, at least at physiological pH values and ionic strengths. Preferably, biological activity occurs under biological assay conditions, i.e., those conditions wherein a monoclonal paratopic molecule useful in this invention binds to the epitope (antigenic determinant) within a pH value range of about 5 to about 9, at ionic strengths such as that of distilled water to that of about one molar sodium chloride, and at temperatures of about 4° C. to about 45° C. The monoclonal paratopic molecules useful herein are all biologically active.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

A "chimeric gene" refers to a sequence of DNA in which nucleotide sequences not naturally occurring together are linked.

A "clone" is a population of cells derived from a single cell or common ancestor by mitosis. A "cell line" is a derivative of a primary cell culture that is capable of stable growth in vitro for many generations.

"Deoxyribonucleic Acid (DNA)" is the molecular basis of heredity. DNA consists of a polysugar-phosphate backbone from which the purines and pyrimidines project. Bonds between the phosphate molecule and carbon 3 and carbon 5 of adjacent deoxyribose molecules form the backbone. The nitrogenous base extends from carbon 1 of each sugar. According to the Watson-Crick model, DNA forms a double helix that is held together by hydrogen bonds between specific pairs of bases (thymine to adenine and cytosine to guanine). Each strand in the double helix is complementary to its partner strand in terms of its base sequence.

A DNA "coding sequence" or a "nucleotide sequence encoding" a particular protein, is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence.

A "DNA construct" is a DNA molecule, or a clone of such a molecule, either single- or double-stranded that has been modified through human intervention to contain segments of DNA combined and juxtaposed in a manner that as a whole would not otherwise exist in nature.

"ELISA" refers to an enzyme-linked immunosorbent assay that employs an antigen or antibody bound to a solid phase and an enzyme-antibody or enzyme-antigen conjugate to detect and quantify the amount of antigen or antibody present in a sample. A description of the ELISA technique is found in U.S. Pat. No. 3,654,090, issued Apr. 4, 1972, U.S. Pat. No. 3,850,752, issued Nov. 26, 1974, and U.S. Pat. No. 4,016,043, issued Apr. 5, 1977, all to Schuurs, et al., which are incorporated herein by reference.

"Immunoreactant" as used herein refers to the product of an immunological reaction; i.e., that entity produced when an antibody or a molecule containing a paratope immunologically binds an antigen.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"hBub1 Allele" refers to normal alleles of the hBub1 locus as well as alleles carrying variations that predispose individuals to develop cancer of many sites including, for example, breast, ovarian, colorectal and prostate cancer. Such predisposing alleles are also called "hBub1 susceptibility alleles".

"hBub1 Locus," "hBub1 Gene," "hBub1 Nucleic Acids" or "hBub1 Polynucleotide" each refer to polynucleotides, all of which are in the hBub1 region, that are likely to be expressed in normal tissue, certain alleles of which predispose an individual to develop breast, ovarian, colorectal and prostate cancers. Mutations at the hBub1 locus may be involved in the initiation and/or progression of other types of tumors. The locus is indicated in part by mutations that predispose individuals to develop cancer. These mutations fall within the hBub1 region described infra. The hBub1 locus is intended to coding sequences, intervening sequences and regulatory elements controlling transcription and/or translation. The hBub1 locus is intended to include all allelic variations of the DNA sequence.

These terms, when applied to a nucleic acid, refer to a nucleic acid which encodes a hBub1 polypeptide, fragment, homolog or variant, including, e.g., protein fusions or deletions. The nucleic acids of the present invention will possess a sequence that is either derived from, or substantially similar to a natural hBub1-encoding gene or one having substantial homology with a natural hBub1-encoding gene or a portion thereof. The coding sequence for a hBub1 polypeptide is shown in SEQ ID NO: 1 and the amino acid sequence of hBub1 is shown GenBank accession NO: AF043294 and in SEQ ID NO:2.

"hBub1 Region" refers to a portion of human chromosome 2q12–13 bounded by the micro-satellite markers D2S293 and D2S121. This region contains the hBub1 locus, including the hBub1 gene.

As used herein, the terms "hBub1 locus," "hBub1 allele" and "hBub1 region" all refer to the double-stranded DNA comprising the locus, allele, or region, as well as either of the single-stranded DNAs comprising the locus, allele or region. As used herein, a "portion" of the hBub1 locus or region or allele is defined as having a minimal size of at least about eight nucleotides, or preferably about 15 nucleotides, or more preferably at least about 25 nucleotides, and may have a minimal size of at least about 40 nucleotides.

"hBub1 protein" or "hBub1 polypeptide" refer to a protein or polypeptide encoded by the hBub1 locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native hBub1 sequence, preferably in excess of about 90%, and more preferably at least about 95% homologous. Also included are proteins encoded by DNA which hybridize under high or low stringency conditions, to hBub1-encoding nucleic acids and closely related polypeptides or proteins retrieved by antisera to the hBub1 protein(s).

The hBub1 polypeptide of the present invention also includes conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Two or more DNA coding sequences are said to be "joined" when, as a result of in-frame fusions between the DNA coding sequences or as a result of the removal of intervening sequences by normal cellular processing, the DNA coding sequences are translated into a polypeptide fusion.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems. The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like.

"Nucleic Acid Hybridization" is a method for using the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitrocellulose filter. In the Southern hybridization procedure, the latter situation occurs. The DNA of the individual to be tested is digested with a restriction endonuclease, fractionated by agarose gel electrophoresis, converted to the single-stranded form, and transferred to nitrocellulose paper, making it available for reannealing to the hybridization probe. A "hybridization Probe" is used to visualize a particular DNA sequence in the Southern hybridization procedure using a labeled DNA molecule or hybridization probe that is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. Molecular cloning of a specific DNA sequence from the human genome generally produces the hybridization probe.

"Oligonucleotides" refers to either a single stranded polydeoxynucleotide or two complementary polydeoxynucleotide strands that may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated. "Probes" refers to isolated polynucleotide attached to a label or reporter molecule and may be used to isolate other polynucleotide sequences, having sequence similarity by standard methods. Polynucleotide polymorphisms associated with hBub1 alleles which predispose to certain cancers or are associated with most cancers are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. Since such indications identify neutral DNA polymorphisms as well as mutations, these indications need further analysis to demonstrate detection of a hBub1 susceptibility allele.

Probes for hBub1 alleles may be derived from the sequences of the hBub1 region or its cDNAs. The probes may be of any suitable length, which span all or a portion of the hBub1 region, and which allow specific hybridization to the hBub1 region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art. Portions of the polynucleotide sequence having at least about eight nucleotides, usually at least about 15 nucleotides, and fewer than about 6 kb, usually fewer than about 1.0 kb, from a polynucleotide sequence encoding hBub1 are preferred as probes. The probes may also be used to determine whether mRNA encoding hBub1 is present in a cell or tissue.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, fusion proteins and the like. "Native" proteins or polypeptides refer to proteins or polypeptides recovered from a source occurring in nature. Thus, the term "native hBub1" would include naturally occurring hBub1 and fragments thereof.

"Protein modifications or fragments" are provided by the present invention for hBub1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}$P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See, e.g., Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of hBub1 polypeptides. Immunological activities include both immunogenic function in a target immune system, as well as sharing of immunological epitopes for binding, serving as either a competitor or substitute antigen for an epitope of the hBub1 protein. As used herein, "epitope" refers to an antigenic determinant of a polypeptide. An epitope could comprise three amino acids in a spatial conformation that is unique to the epitope. Generally, an epitope consists of at least five such amino acids, and more usually consists of at least 8–10 such amino acids. Methods of determining the spatial conformation of such amino acids are known in the art.

The present invention also provides for fusion polypeptides, comprising hBub1 polypeptides and fragments. Homologous polypeptides may be fusions between two or more hBub1 polypeptide sequences or between the sequences of hBub1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial beta-galactosidase, trpE, protein A, beta-lactamase, alpha amylase, alcohol dehydrogenase and yeast alpha mating factor. See, e.g., Godowski et al., 1988. Fusion proteins will typically be made by either recombinant nucleic acid methods, as described below, or may be chemically synthesized. Techniques for the synthesis of polypeptides are described, for example, in Merrifield, 1963.

The term "recombinant" refers to a nucleic acid sequence that is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide.

"Restriction Fragment Length Polymorphism (RFLP)" refers to when the genomic DNA of two individuals in a population will differ in sequence at many sites either as a result of change in bases or insertions or deletions of sequences. When these differences occur in the recognition site for a restriction endonuclease, then a polymorphism in the length of restriction fragments produced by digestion of the DNA of the two individuals will result. For example, the hypothetical pattern of restriction fragments produced by digestion of A and B with restriction enzyme EcoRI exhibits a polymorphism, since the DNA of individual A yields fragment c of length 600 base pairs and fragment d of length 400 base pairs, while DNA of individual B gives a single fragment e of length 1,000 base pairs. As used herein, a polymorphism is also referred to as a "pattern."

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement.

Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968. Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type hBub1 nucleic acid or wild-type hBub1 polypeptide. The modified polypeptide will be substantially homologous to the wild-type hBub1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type hBub1 polypeptide. Alternatively, the similarity of function (activity) of the modified polypeptide may be higher than the activity of the wild-type hBub1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type hBub1 gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

The present invention provides a cloned cDNA encoding full-length human Bub1 protein (hBub1). Our analysis shows that hBub1 has several domains including a MAD3 homologous region at the N-terminus. Expression of hBub1 is strongly associated with cells/tissues with a high mitotic index. We have shown that hBub1 protein is localized at centromere-kinetochore and that appears to be an important component of the spindle checkpoint pathway. In addition, the hBub1 gene is mapped to chromosome 2q12–13, a region implicated in the development of certain genetic diseases.

The present invention describes a cDNA encoding a full-length human spindle checkpoint kinase named hBub1. Analysis of the deduced amino acid sequence suggests that hBub1 has a kinase domain and an N-terminal region highly homologous to yeast MAD3. The homology between yeast Bub1 and yeast MAD3 has been reported before (9). In addition, hBub1 contains a region sharing homology to muKIF4, a kinesin-like protein in mouse (23). MAD3 is known to be involved in mitotic checkpoint response pathways (6,9), and muKIF4 is associated with microtubules (23). Thus, while not wishing to be bound by the hypothesis, the structural homology of hBub1 to these two proteins suggests that hBub1 may functionally and physically interact with other proteins in the mitotic checkpoint and, thus, serve as a key component in the checkpoint response. Identification of the in vivo substrate(s) of hBub1 would open a new avenue of research for study of the spindle checkpoint.

The hBub1 gene expression is correlated with cells/tissues with a high mitotic index. Among over a dozen or more tumor-derived cell lines examined, hBub1 mRNA expression was detected in all these cell lines. Activation of yeast BUB1 halts mitotic progression when chromosomes fail to align correctly during mitosis as a result of microtubule disruption or chromosome abnormalities (6,8,9). It is reasonable, therefore, to speculate that hBub1 functions as a mitosis-safeguard protein to ensue the order of progression of mitotic events. Therefore, it is conceivable that hBub1 may not be required for quiescent or differentiated cells. Indeed, this notion is supported by our observations that (i) fully differentiated primary tissues such as brain, muscle, heart, etc. express no detectable levels of hBub1 transcripts and that (ii) hBub1 mRNA expression is rapidly turned off when Dami cells are undergoing differentiation.

Many human genes involved in cell cycle checkpoint controls are important for suppression of tumor growth and determination of chemo-sensitivity of tumor cells. For example, p53 tumor suppressor and ATM gene product regulate the G1/S checkpoint and DNA damage checkpoint, respectively (27,28). Structural abnormalities in these genes predispose a cell to neoplastic transformation (28). Recently, human chk1 gene has been cloned and characterized (29). The chk1 gene product, a serine/threonine kinase, functions as a key component that links the DNA damage checkpoint to the cell-cycle engine (1). The human chk1 gene has been mapped to 11q24, a locus shown to contain a potential tumor suppressor (29). Therefore, similar to the scenario of unrepaired DNA, unchecked chromosome segregation may lead to aneuploidy or genomic instability in daughter cells, which may play an important part in the malignant transformation process. It has been shown that dominant negative mBub1 is capable of suppression of spindle checkpoint and fails to initiate apoptosis when needed (15).

Of particular interest is the detection of deletions in the hBub1 gene, e.g. by amplification of the region and size fractionation of the amplification product; restriction mapping, etc. Screening of tumors may also be based on the functional or antigenic characteristics of the protein. Immunoassays designed to detect the normal or abnormal hBub1 protein may be used in screening. Alternatively, functional assays, e.g., assays based on detecting changes in the spindle checkpoint pathway mediated by hBub1, may be performed.

The hBub1 gene may also be used for screening of patients suspected of having a genetic predisposition to hBub1-associated tumors, where the presence of a mutated hBub1 sequence confers an increased susceptibility to cancer. Diagnosis is performed by protein, DNA sequence, PCR screening, or hybridization analysis of any convenient sample from a patient, e.g. biopsy material, blood sample, scrapings from cheek, etc. A typical patient genotype will have an oncogenic mutation on one chromosome. When the normal copy of hBub1 is lost, leaving only the reduced function mutant copy, abnormal cell growth is the result.

Prenatal diagnosis may be performed, particularly where there is a family history of the disease, e.g. an affected parent or sibling. A sample of fetal DNA, such as an amniocentesis sample, fetal nucleated or white blood cells isolated from maternal blood, chorionic villus sample, etc. is analyzed for the presence of the predisposing mutation. Alternatively, a protein based assay, e.g. functional assay or immunoassay, is performed on fetal cells known to express hBub1.

The DNA sequence encoding hBub1 may be cDNA or genomic DNA or a fragment thereof. The term "hBub1 gene" shall be intended to mean the open reading frame encoding specific hBub1 polypeptides, as well as adjacent 5' and 3' non-coding nucleotide sequences involved in the regulation of expression, up to about 1 kb beyond the coding region, in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons, 3' and 5' non-coding regions. Normally mRNA species have contiguous exons, with the intervening introns deleted, to create a continuous open reading frame encoding hBub1.

The genomic hBub1 sequence has non-contiguous open reading frames, where introns interrupt the coding regions. A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb of flanking genomic DNA at either the 5' or 3' end of the coding region. The genomic DNA may be isolated as a fragment of 20 kbp or smaller; and substantially free of flanking chromosomal sequence.

The nucleic acid compositions of the subject invention encode all or a part of the subject polypeptides. Fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful for hybridization screening, etc. Larger DNA fragments, i.e. greater than 100 bp, usually greater than 500 bp, are useful for production of the encoded polypeptide. Single stranded oligonucleotides of from about 18 to 35 nt in length are useful for PCR amplifications. For use in amplification reactions, such as PCR, a pair of primers will be used. The exact composition of the primer sequences is not critical to the invention, but for most applications the primers will hybridize to the subject sequence under stringent conditions, as known in the art. It is preferable to chose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the hBub1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered. Alterations in hBub1 nucleic acid include intragenic mutations (e.g., point mutation, nonsense (stop), missense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Alterations in hBub1 nucleic acid may be detected as a truncated protein product. Standard SDS-PAGE and/or immunoprecipitation analysis and/or Western blot analysis can analyze such proteins, for example. In addition, the in vitro synthesized (IVS) protein assay as described in the present examples can be used to analyze hBub1 protein product.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

The hBub1 genes are isolated and obtained in substantial purity, generally as other than an intact mammalian chromosome. Usually, the DNA will be obtained substantially free of other nucleic acid sequences that do not include a hBub1 sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying other genes. Mammalian homologs have substantial sequence similarity to the subject sequences, i.e. at least 75%, usually at least 90%, more usually at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215:403–10.

Nucleic acid can isolate homologous or related genes. The source of homologous genes may be any mammalian species, e.g. primate species; murines, such as rats and mice; canines; felines; bovines; ovines; equines; etc.

The DNA may also be used to identify expression of the gene in a biological specimen. The manner in which one probes cells for the presence of particular nucleotide sequences, as genomic DNA or RNA, is well-established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, and then probed with a fragment of the subject DNA as a probe. Other techniques may also find use. Detection of mRNA having the subject sequence is indicative of hBub1 gene expression in the sample.

The subject nucleic acid sequences may be modified for a number of purposes, particularly where they will be used intracellularly, for example, by being joined to a nucleic acid cleaving agent, e.g. a chelated metal ion, such as iron or chromium for cleavage of the gene; as an antisense sequence; or the like. Modifications may include replacing oxygen of the phosphate esters with sulfur or nitrogen, replacing the phosphate with phosphoramide, etc.

A number of methods are available for analyzing genomic DNA sequences for the presence of mutations. Where large amounts of DNA are available, the genomic DNA is used directly. Alternatively, the region of interest is cloned into a suitable vector and grown in sufficient quantity for analysis, or amplified by conventional techniques, such as the polymerase chain reaction (PCR). The use of the polymerase chain reaction is described in Saiki et al. (1985) Science 239:487, and a review of current techniques may be found in. Sambrook, et al. Molecular Cloning: A Laboratory Manual, CSH Press 1989, pp. 14.2–14.33.

PCR is particularly useful for detection of oncogenic mutations. In many cases such mutations involve a deletion at the hBub1 locus. For example, primers specific for hBub1 are used to amplify all or part of the gene. The amplification products are then analyzed for size, where a deletion will result in a smaller than expected product. Where the deletion is very large, there may be a complete absence of the specific amplification product. Alternatively, analysis may be performed on mRNA from a cell sample, where the RNA is converted to cDNA, and then amplified (RT-PCR).

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N', N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Dideoxy or other methods may sequence the amplified or cloned fragment, and the sequence of bases compared to the normal hBub1 sequence. Hybridization with the variant, oncogenic sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilized on a solid support, as described in WO 95/11995, may also be used as a means of detecting the presence of variant sequences. Alternatively, where an oncogenic mutation creates or destroys a recognition site for a restriction endonuclease, the fragment is digested with that endonuclease, and the product's size fractionated to determine whether the fragment was digested. Fractionation is performed by gel electrophoresis, particularly acrylamide or agarose gels.

The subject nucleic acids can be used to generate transgenic animals or site specific gene modifications in cell lines. The modified cells or animals are useful in the study of hBub1 function and regulation. For example, a series of small deletions and/or substitutions may be made in the hBub1 gene to determine the role of different exons in oncogenesis, signal transduction, etc. One may also provide for expression of the hBub1 gene or variants thereof in cells or tissues where it is not normally expressed or at abnormal times of development. In addition, by providing expression of hBub1 protein in cells in which it is otherwise not normally produced, one can induce changes in cell behavior.

DNA constructs for homologous recombination will comprise at least a portion of the hBub1 gene with the desired genetic modification, and will include regions of homology to the target locus. Alternatively, constructs may that do not target to the native locus, but integrate at random sites in the genome. Conveniently, markers for positive and negative selection are included. Methods for generating cells having targeted gene modifications through recombination are known in the art. For various techniques for transfecting mammalian cells, see Keown et al. (1990) Methods in Enzymology 185:527–537.

The subject gene may be employed for producing all or portions of the hBub1 protein. Peptides of interest include the MAD3-homologous domain (aa 30–191), the kinesin-like domain (aa 212–364) and the kinase domain (aa 786–1085). For expression, an expression cassette may be employed, providing for a transcriptional and translational initiation region, which may be inducible or constitutive, the coding region under the transcriptional control of the transcriptional initiation region, and a transcriptional and translational termination region. Various transcriptional initiation regions may be employed which are functional in the expression host.

The peptide may be expressed in prokaryotes or eukaryotes in accordance with conventional ways, depending upon the purpose for expression. For large scale production of the protein, a unicellular organism or cells of a higher organism, e.g. eukaryotes such as vertebrates, particularly mammals, may be used as the expression host, such as *E. coli, S. cerevisiae*, and the like. In many situations, it may be desirable to express the hBub1 gene in a mammalian host, whereby the hBub1 protein will be glycosylated.

With the availability of the protein in large amounts by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. By pure is intended essentially free of other proteins, as well as cellular debris.

hBub1 polypeptides are useful in the investigation of the spindle checkpoint pathway, which is essential for cell proliferation. The normal and mutated forms of hBub1 polypeptides may be used for binding assays with other proteins, to detect changes in its phosphorylation, etc. that may affect its activity and the checkpoint pathway.

The polypeptide is used for the production of antibodies, where short fragments provide for antibodies specific for the particular polypeptide, whereas larger fragments or the entire gene allow for the production of antibodies over the surface of the polypeptide or protein. Antibodies may be raised to the normal or mutated forms of hBub1. The MAD3-homologous, kinesin-like and the kinase domains of the protein are of interest as epitopes, particularly to raise antibodies that recognize common changes found in oncogenic hBub1. Antibodies may be raised to isolated peptides corresponding to these domains, or to the native protein. Antibodies that recognize hBub1 are useful in diagnosis, typing and staging of human tumors.

Preparation of Antibodies

Antibodies are prepared in accordance with conventional ways, where the expressed polypeptide or protein may be used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen may be isolated, the splenocytes immortalized, and then screened for high affinity antibody binding. The immortalized cells, e.g. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutigenized by cloning in *E. coli*, and the heavy and light chains may be mixed to further enhance the affinity of the antibody.

The antibodies find particular use in diagnostic assays for carcinomas and other tumors associated with mutations in hBub1. Staging, detection and typing of tumors may utilize a quantitative immunoassay for the presence or absence of normal hBub1. Alternatively, the presence of mutated forms of hBub1 may be determined. A reduction in normal hBub1 and/or presence of abnormal hBub1 is indicative that the tumor is hBub1-associated.

A sample is taken from a patient suspected of having an hBub1-associated tumor. Samples, as used herein, include biological fluids such as blood, cerebrospinal fluid, tears, saliva, lymph, dialysis fluid and the like, organ or tissue culture derived fluids; and fluids extracted from physiological tissues. Also included in the term are derivatives and fractions of such fluids. Biopsy samples are of particular interest, e.g. carcinoma samples, organ tissue fragments, etc. Where metastasis is suspected, blood samples may be preferred. The number of cells in a sample will generally be at least about $10^3$, usually at least $10^4$, more. Usually a lysate of the cells is prepared.

Diagnosis may be performed by a number of methods. The different methods all determine the absence or presence of normal or abnormal hBub1 in patient cells suspected of having a mutation in hBub1. For example, detection may utilize staining of histological sections, performed in accordance with conventional methods. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well-known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including microscopy, spectrophometry, scintillation counting, etc.

An alternative method for diagnosis depends on the in vitro detection of binding between antibodies and hBub1 in a lysate. Measuring the concentration of hBub1 binding in a sample or fraction thereof may be accomplished by a variety of specific assays. A conventional sandwich type assay may be used. For example, a sandwich assay may first attach hBub1-specific antibodies to an insoluble surface or support. The particular manner of binding is not crucial so long as it is compatible with the reagents and overall methods of the invention. They may be bound to the plates covalently or non-covalently, preferably non-covalently.

Patient sample lysates are then added to separately assayable supports (for example, separate wells of a microtiter plate) containing antibodies. Preferably, a series of standards, containing known concentrations of normal and/or abnormal hBub1 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind hBub1 with sufficient specificity such that it can be distinguished from other components present. The second antibodies may be labeled to facilitate direct, or indirect quantification of binding. Examples of labels that permit direct measurement of second receptor binding include radiolabels, such as 3H or 125I, fluorescers, dyes, beads, chemiluminescers, colloidal particles, and the like. Examples of labels that permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, a time from about 0.1 to 3 hr is sufficient, usually 1 hr sufficing.

After the second binding step, the insoluble support is again washed free of non-specifically bound material. The signal produced by the bound conjugate is detected by conventional means. Where an enzyme conjugate is used, an appropriate enzyme substrate is provided so a detectable product is formed.

Other immunoassays are known in the art and may find use as diagnostics. Western blots may be performed on protein gels or protein spots on filters, using a detection system specific for hBub1 as desired, conveniently using a labeling method as described for the sandwich assay.

The term "agent" as used herein describes any molecule, protein, or pharmaceutical with the capability of altering or mimicking the physiological function of hBub1. Generally a plurality of assay mixtures are run in parallel with different agent concentrations to obtain a differential response to the various concentrations. Typically, one of these concentrations serves as a negative control, i.e. at zero concentration or below the level of detection.

Other assays of interest detect agents that mimic hBub1 function. For example, candidate agents are added to cells that lack functional hBub1, and screened for the ability to reproduce hBub1 function, e.g. prevent growth of 3T3 cells in soft agar.

The compounds having the desired pharmacological activity may be administered in a physiologically acceptable carrier to a host for treatment of cancer attributable to a defect in tsg101 function. The inhibitory agents may be administered in a variety of ways, orally, topically, parenterally e.g. subcutaneously, intraperitoneally, intravascularly, etc. Topical treatments are of particular interest. Depending upon the manner of introduction, the compounds may be formulated in a variety of ways. The concentration of therapeutically active compound in the formulation may vary from about 0.1 to about 100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The gene may also be used for gene therapy. Vectors useful for introduction of the gene include plasmids and viral vectors. Of particular interest are retroviral-based vectors, e.g. moloney murine leukemia virus and modified human immunodeficiency virus; adenovirus vectors, etc. Gene therapy may be used to treat cancerous lesions, an affected fetus, etc., by transfection of the normal gene into suitable cells. A wide variety of viral vectors can be employed for transfection and stable integration of the gene into the genome of the cells. Alternatively, micro-injection may be employed, fusion, or the like for introduction of genes into a host cell. See, for example, Dhawan et al. (1991) Science 254:1509–1512 and Smith et al. (1990) Molecular and Cellular Biology 3268–3271.

PREPARATION OF RECOMBINANT hBub1

Large quantities of the polypeptides of the present invention may be prepared by expressing the hBub1 nucleic acids or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of hBub1 polypeptides.

Antisense polynucleotide sequences are useful in preventing or diminishing the expression of the hBub1 locus, as will be appreciated by those skilled in the art. For example, polynucleotide vectors containing all or a portion of the hBub1 locus or other sequences from the hBub1 region (particularly those flanking the hBub1 locus) may be placed under the control of a promoter in an antisense orientation and introduced into a cell. Expression of such an antisense construct within a cell will interfere with hBub1 transcription and/or translation and/or replication.

The probes and primers based on the hBub1 gene sequences disclosed herein are used to identify homologous hBub1 gene sequences and proteins in other species. These hBub1 gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of a hBub1 allele predisposing an individual to cancer, a biological sample such as blood is prepared and analyzed for the presence or absence of susceptibility alleles of hBub1. In order to detect the presence of neoplasia, the progression toward malignancy of a precursor lesion, or as a prognostic indicator, a biological sample of the lesion is prepared and analyzed for the presence or absence of mutant alleles of hBub1. Results of these tests and interpretive information are returned to the health care provider for communication to the tested individual.

Diagnostic laboratories may perform such diagnoses, or, alternatively, diagnostic kits are manufactured and sold to health care providers or to private individuals for self-diagnosis.

Initially, the screening method involves amplification of the relevant hBub1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions that promote stable hybrid formation of the target sequence in the probe with the putative targeted sequence in the analyte. The region of the probes that is used to bind to the analyte can be made completely complementary to the targeted region of human chromosome 2q12–14. Therefore, high stringency conditions are desirable in order to prevent false positives. However, conditions of high stringency are used only if the probes are complementary to regions of the chromosome that are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Suitable labels, and methods for labeling probes are known in the art, and include, for example, radioactive labels which may be incorporated by known methods (e.g., nick translation, random priming), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews & Kricka, 1988; Landegren et al., 1988, Mittlin, 1989; U.S. Pat. No. 4,868,105, and in EPO Publication No. 225,807. As noted above, non-PCR based screening assays are also contemplated in this invention. This procedure hybridizes a nucleic acid probe (or an analog such as a methyl phosphonate backbone replacing the normal phosphodiester), to the low level DNA target.

It is also contemplated within the scope of this invention that the nucleic acid probe assays of this invention will employ a cocktail of nucleic acid probes capable of detecting hBub1. Thus, in one example to detect the presence of hBub1 in a cell sample, more than one probe complementary to hBub1 is employed and in particular the number of different probes is alternatively 2, 3, or 5 different nucleic acid probe sequences. In another example, to detect the presence of mutations in the hBub1 gene sequence in a patient, more than one probe complementary to hBub1 is employed where the cocktail includes probes capable of binding to the allele-specific mutations identified in populations of patients with alterations in hBub1. In this embodiment, any number of probes can be used, and will preferably include probes corresponding to the major gene mutations identified as predisposing an individual to colorectal cancer. Some candidate probes contemplated within the scope of the invention include probes that include the allele-specific mutations identified in Tables 11 and 12 and those that have the hBub1 regions corresponding to SEQ NO: 1 both 5' and 3' to the mutation site.

Methods of Use: Peptide Diagnosis and Diagnostic Kits

The neoplastic condition of lesions can also be detected on the basis of the alteration of wild-type hBub1 polypeptide. Such alterations can be determined by sequence analysis in accordance with conventional techniques. More preferably, antibodies (polyclonal or monoclonal) are used to detect differences in, or the absence of hBub1 peptides. The antibodies may be prepared as discussed above. Other techniques for raising and purifying antibodies are well known in the art and any such techniques may be chosen to achieve the preparations claimed in this invention. In a preferred embodiment of the invention, antibodies will immunoprecipitate hBub1 proteins from solution as well as react with hBub1 protein on Western or immunoblots of polyacrylamide gels. In another preferred embodiment, antibodies will detect hBub1proteins in paraffin or frozen tissue sections, using immunocytochemical techniques.

Preferred embodiments relating to methods for detecting hBub1 or its mutations include enzyme linked immunosorbent assays (ELISA), radioimmunoassays (RIA), immunoradiometric assays (IRMA) and immunoenzymatic assays (EMA), including sandwich assays using monoclonal and/or polyclonal antibodies. U.S. Pat. Nos. 4,376,110 and 4,486,530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., hBub1 polypeptide) or, for example, of the phosphorylated hBub1 or hBub1-agonist complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., hBub1 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idio-typic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved hBub1 polypeptide activity or stability or which act as inhibitors, agonists, antagonists, etc. of hBub1 polypeptide activity. By virtue of the availability of cloned hBub1 sequences, sufficient amounts of the hBub1 polypeptide may be made available to perform such analytical studies as x-ray crystallography. In addition, the knowledge of the hBub1 protein sequence provided herein will guide those employing computer modeling techniques in place of, or in addition to x-ray crystallography.

Methods of Use: Gene Therapy

According to the present invention, a method is also provided of supplying wild-type hBub1 function to a cell that carries mutant hBub1 alleles. Supplying such a function should suppress neoplastic growth of the recipient cells. The wild-type hBub1 gene or a part of the gene may be introduced into the cell in a vector such that the gene remains extrachromosomal. In such a situation, the cell from the extrachromosomal location will express the gene. If a gene fragment is introduced and expressed in a cell carrying a mutant hBub1 allele, the gene fragment should encode a part of the hBub1 protein, which is required for non-neoplastic growth of the cell. More preferred is the situation where the wild-type hBub1 gene or a part thereof is introduced into the mutant cell in such a way that it recombines with the endogenous mutant hBub1 gene present in the cell. Such recombination requires a double recombination event that results in the correction of the hBub1 gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the routineer. Cells transformed with the wild-type hBub1 gene can be used as model systems to study cancer remission and drug treatments that promote such remission.

As generally discussed above, the hBub1 gene or fragment, where applicable, may be employed in gene therapy methods in order to increase the amount of the expression products of such genes in cancer cells. Such gene therapy is particularly appropriate for use in both cancerous and pre-cancerous cells, in which the level of hBub1 polypeptide is absent or diminished compared to normal cells. It may also be useful to increase the level of expression of a given hBub1 gene even in those tumor cells in which the mutant gene is expressed at a "normal" level, but the gene product is not fully functional.

Gene therapy would be carried out according to generally accepted methods, for example, as described by Friedman, 1991. Cells from a patient's tumor would be first analyzed by the diagnostic methods described above, to ascertain the production of hBub1 polypeptide in the tumor cells. A virus or plasmid vector (see further details below), containing a copy of the hBub1 gene linked to expression control elements and capable of replicating inside the tumor cells, is prepared. Suitable vectors are known, such as disclosed in U.S. Pat. No. 5,252,479 and PCT published application WO 93/07282. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller el al, 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al, 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolffet al., 1991; Wagner et al., 1990, Wagner et al., 1991; Cotten et al., 1990; Curiel et al., 1991a; Curiel et al., 1991b). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene therapy methods as described herein can be performed in vivo or ex vivo. In addition, it may be preferable to remove the majority of a tumor prior to gene therapy, for example surgically or by radiation.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a hBub1 sequence (including promoter region) of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences that can be inserted into the retroviral genome to allow target specific delivery of the retroviral vector containing the hBub1 sense or antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence, which enables the packaging mechanism to recognize an RNA transcript for encapsidation. Helper cell lines which have deletions of the packaging signal include but are not limited to PSI 2, PA317 and PA12, for example. These cell lines produce empty virions, since no genome is packaged. If a retroviral vector is introduced into other genes of interest replace such cells in which the packaging signal is intact, but the structural genes, the vector can be packaged and vector virion produced.

Another targeted delivery system for hBub1 polynucleotide is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

Methods of Use: Peptide Therapy

Peptides that have hBub1 activity can be supplied to cells that carry mutant or missing hBub1 alleles. The sequence of the hBub1 protein is disclosed (GenBank Accession NO: AF043294). Protein can be produced by expression of the cDNA sequence in bacteria, for example, using known expression vectors. Alternatively, hBub1 polypeptide can be extracted from hBub1-producing mammalian cells. In addition, the techniques of synthetic chemistry can be employed to synthesize hBub1 protein. Any of such techniques can provide the preparation of the present invention which comprises the hBub1 protein. The preparation is substantially free of other human proteins. This is most readily accomplished by synthesis in a microorganism or in vitro.

Active hBub1 molecules can be introduced into cells by microinjection or by use of liposomes, for example. Alternatively, cells may take up some active molecules, actively or by diffusion. Extracellular application of the hBub1 gene product may be sufficient to affect tumor growth. Supply of molecules with hBub1 activity should lead to partial reversal of the neoplastic state. Other molecules with hBub1 activity (for example, peptides, drugs or organic compounds) may also be used to effect such a reversal. Modified polypeptides having substantially similar function are also used for peptide therapy.

Methods of Use: Transformed Hosts

Similarly, cells and animals that carry a mutant hBub1 allele can be used as model systems to study and test for substances which have potential as therapeutic agents. The cells are typically cultured epithelial cells. These may be isolated from individuals with hBub1 mutations, either somatic or germline. Alternatively, the cell line can be engineered to carry the mutation in the hBub1 allele, as described above. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant hBub1 alleles, usually from a second animal species, as well as insertion of disrupted homologous genes. Alternatively, the endogenous hBub1 gene(s) of the animals may be disrupted by insertion or deletion mutation or other genetic alterations using conventional techniques (Capecchi, 1989; Valancius and Smithies, 1991; Hasty et al., 1991, Shinkai et al., 1992; Mombaerts et al., 1992; Philpott et al., 1992; Snouwaert et al., 1992; Donehower et al., 1992). After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

EXPERIMENTAL PROCEDURES

Materials: Restriction enzymes, T4 DNA ligase, DNA-labeling kit, 5' and 3' RACE (rapid amplification of cDNA end) kits, various culture media (RPMI1640, DMEM), and antibiotics (penicillin-streptomycin) were purchased from GIBCO/BRL (Grand Island, N.Y.). K562, GM00637D, Dami, A549, and PC-3 cell lines were purchased from American Type Cell Collection (Rockville, Md.). MCF-7 and DU145 cell lines were kindly provided by Dr. Peter Reissman. The GeneClean system was from Bio101 Inc (Vista, Calif.). A multiple tissue master dot blot was purchased from Clontech (Palo Alto, Calif.). The pT7Blue plasmid was obtained from Novagen Inc. (Madison, Wis.). and Dami cell lines were cultured in RPMI1640 medium; A549, MCF-7, DU145, PC3, and GM00637D cell lines were cultured in DMEM. A549 cells were used for synchronization studies. A549 cells in G1 phase were obtained by culture in methionine-free DMEM containing 10% FBS for 48 hours. A549 cells synchronized at the G1/S boundary were achieved by sequential culture in medium containing aphidicolin phorbol 12-myristate 13-acetate (PMA, 10 mM) for various time (1, 2, 4, 8, 12, and 24 hours). At the end of treatment, cells were collected for RNA isolation.

RNA isolation and PCR amplification. Total RNA was isolated, according to the protocol, from various cell lines, using a kit obtained from Tel-Test Inc. Reverse transcriptase-mediated polymerase chain reaction (RT-PCR) was performed on total RNA from Dami cells using a SUPERSCRIPTTM PREAMPLIFICATION system purchased from GIBCO/BRL. The PCR products were analyzed on agarose gels, and DNA bands were excised and eluted from the gels using the GeneClean system. The eluted PCR products were directly cloned into pT7Blue vector for sequencing analysis.

RACE procedure. The 5' RACE procedure was carried out according to the supplier's protocol. Two hBub1-specific primers (antisense) were synthesized and named hBub1-P1 (5'CTCTGAAGGACAGCACTGGA 3') and hBub1-P2 (5'GTACAGAGGGGATGACAGGG3'). First strand cDNA was synthesized from K562 total RNA, using the primer hBub1-P2. This synthesized cDNA was used for a TdT-tailing reaction and, then, for PCR amplification using an anchor primer provided in the kit and hBub1-P1. The specificity of PCR amplification was confirmed by Southern blotting analysis. The amplified products were eluted from agarose gels and cloned into the pT7Blue vector for sequencing analysis. The 3'RACE procedure was also done according to the supplier's protocol. First strand cDNA was synthesized from K562 total RNA using poly T adapter primer. Amplification was performed using a hBub1 primer (5'GATTGACCTGGGTCAGAGTA3') and a universal amplification primer. Amplified products were cloned into a pT7Blue vector for sequencing analysis.

Dot and Northern blotting. Approximately equal amounts of total RNA (10 bovine serum albumin, 15% formamide] at 65° C. for 4 hr. The blots were then hybridized overnight at 65° C. in a fresh hybridization mixture containing a 32P-labeled hBub1 cDNA probe. After hybridization, the blots were washed three times at 65° C. in a washing buffer (40 mM Na2HPO4NaH2PO4 (pH 7.5), 1 mM EDTA, 1% SDS) and autoradiographed. A multiple-tissue dot blot was hybridized overnight with a 32P-labeled hBub1 probe according to the supplier's protocol. Specific signals detected on autoradigraphs were quantified using an image scanner (IMAGER DENSITOMETER GS-700, BioRad, Calif.).

Western blotting. Polyclonal anti-hBub1 peptide antisera were raised in rabbits. The peptide corresponding to amino acids EAELGVEACRLTDTD (residues 690 to 704) is shown in FIG. 1. For Western blotting, treated cells were collected and lysed in buffer [50 mM Tris-HCl (pH 7.5), 150 mM NaCl, 1% NP-40, 1 mM EDTA, 1 mM Na3VO4, 1 mM PMSF, 10 were first probed with an anti-hBub1 antibody (in the presence or absence of excess amounts of peptide competitor) and then probed with a goat anti-rabbit antibody conjugated with horseradish peroxidase. The signals were detected by enhanced chemiluminescence (Amersham). Some blots were stripped and reprobed with the normal rabbit serum.

Antibody electroporation. Anti-hBub1 antibody was purified from anti-hBub1 rabbit serum using protein A sepharose resins (Pharmacia). IgGs from normal rabbit serum are purified in a similar manner. Antibody electroporation was as described (13). Briefly, A549 cells, resuspended in PBS at a cell density of 4×105/ml, were electroporated with purified IgGs as a control at 300 mV and 250 (F. After electroporation, the cells were aliquoted and placed a 4-well chamber slide and a 6-well tissue culture dish with fresh culture medium. The cells were incubated overnight and then treated with nocodazole (200 nM) for 18 hours (unless otherwise specified). At the end of incubation, mitotic (rounded) and interphase (flattened) cells in 6-well culture dishes were counted for each treatment. In addition, the cells in the 4-well chamber slide were stained with DAPI and goat anti-rabbit antibody conjugated to rhodamine and examined under fluorescent microscope. We observed that more than 90% cells that survived electroporation took up IgG, as shown by immunofluorescence.

Immunofluorescence and Fluorescence in situ hybridization (FISH). PC-3 cell line was used for subcellular localization of hBub1 protein since it had a low level of non-specific signals immunoreactive to the anti-hBub1 antibody. Cell fixation and immunofluorescence were performed as described (17). To reduce the background staining, PC-3 cells were treated with 0.5% Triton X100 before fixation. The rabbit anti-hBub1 was used with a dilution of 1:200 and the CREST antiserum was diluted 1:100. All secondary antibodies were obtained from Boehringer Mannheim. Normal rabbit serum (1:200) was used as a control. FISH was performed essentially as described (18, 19). Briefly, lymphocytes isolated from human blood were cultured in (-minimal essential medium (MEM) supplemented with 10% FBS and phytohemagglutinin at 37° C. for 68 to 72 hours. The lymphocyte cultures were treated with bromodeoxyuridine (BrdU, 0.18 mg/ml) to synchronize the cell population. Synchronized cells were washed with serum-free medium to release the block and re-cultured at 37° C. for 6 hr in (-MEM with thymidine (2.5 (g/ml). Cells were harvested, and slides were made using standard procedures including hypotonic treatment, fixation and air-dry. Slides were baked at 55° C. for 1 hr. After RNAse treatment, the slides were denatured in 70% formamide in 2×SSC for 2 min followed by dehydration with ethanol. The biotinylated hBub1 cDNA probe was denatured at 75° C. for 5 min in a hybridization mix consisting of 50% formamide and 10% dextran sulphate. The hBub1 probe was applied to the denatured chromosome slides. Following hybridization overnight, slides were washed for image detection. FISH photograph and the DAPI banding pattern were recorded separately. The assignment of the FISH mapping data with chromosome bands was achieved by superimposing FISH signals on DAPI banded chromosomes.

GenBank Accession number. The GenBank accession number for hBub1 cDNA is AF043294, herein incorporated by reference in its entirety.

RESULTS

It is known that protein kinases are the primary regulators of cell-cycle progression and the effectors of cell-cycle checkpoints (1,3,20). Major cell-cycle checkpoint pathways such as those of DNA and spindle damage checkpoints are thought to be conserved across a wide evolutionary spectrum. Indeed, our search of expressed sequence tag (EST) databases yielded a human DNA fragment approximately 300 base pairs in length (accession number: AA383290) that was significantly homologous to both yeast BUB1 and mBub1. To clone the putative human Bub1 cDNA, two oligonucleotide primers, based on the EST sequence, were made. In addition, four consensus oligonucleotide primers, based on mBub1/BUB1 conserved DNA sequences, were synthesized. Two of the primers correspond to the N-terminal region of mBub1/BUB1, and two correspond to the C-terminal region of mBub1/BUB1. Various primer pairs (one human and one consensus) were used to amplify cDNAs made from K562 mRNA. Two pairs of PCR primers yielded products with expected size; these were cloned into the pT7Blue vector for DNA sequencing analysis. Initial sequencing analyses revealed that sequences from these two PCR fragments are homologous to both yeast BUB1 and mBub1, and we named them as putative human Bub1 (hBub1) fragments. To confirm the identity of the cloned hBub1 fragments, additional hBub1 primers were made, according to the newly-derived hBub1 sequences, to re-amplify K562 cDNAs. Again, PCR products of expected size were amplified. Using this strategy, a majority (75%) of hBub1 cDNA sequence was obtained as compared with its mRNA size. The confirmed hBub1 cDNA sequence predicted a single, long, open reading frame. However, the initiating codon ATG for translation and the termination codon were absent.

The 5' RACE method as described in Experimental Procedures was then employed to obtain the remainder of the 5' end of hBub1 cDNA. Amplified cDNA fragments were analyzed by agarose gel electrophoresis, eluted from agarose, and cloned into pT7Blue plasmid vector. Plasmid DNA isolated from selected transformants were sequenced, revealing an insert that extended the 5' end of hBub1 by about 300 base pairs (bp). Deduced amino acid analysis revealed an in-frame ATG codon coding for a putative translation initiation amino acid methionine. There is a TGGCC sequence preceding the ATG codon, closely resembling the Kozak sequence CCGCC, which is optimal for translation initiation (21).

The 3' RACE method was employed in a similar manner to obtain the missing 3' hBub1 cDNA sequence. A major PCR fragment of 500 bp was amplified. Subsequent cloning and sequencing analyses revealed that the 3' RACE fragment contained an in-frame stop codon and a poly A stretch located 22 nucleotides downstream from the stop codon. The complete nucleotide sequence as well as the deduced amino acid sequence are shown in FIG. 1. The long open reading frame encodes a protein of 1085 amino acids with a calculated molecular mass of 122 kDa. The kinase domain resides in the C-terminal third region of the predicted hBub1 protein. The ATP-binding site (GEGAFAQV) in the kinase domain (double-underlined FIG. 1) agrees very well with the consensus site [GXGXXG(S/A)V] described previously (22). There is a putative nuclear targeting signal (single underlined, FIG. 1) at the N-terminal region of the predicted amino acid sequence. In addition, there is one copy of a consensus polyadenylation signal AATAAA located 20 nucleotides 5' to the poly A tail.

A sequence comparison with databanks reveals that hBub1 shares the strongest residue identity (72%) with murine Bub1. It is also significantly homologous to BUB1 protein of budding yeast with a 23% residue identity. The residue identity between hBub1 and mBub1 (or yeast BUB1) is not confined to the kinase domain, suggesting a conserved biological function for this family of genes. Interestingly, the N-terminal part (161 amino acid residues) shows a 26% amino acid identity to yeast MAD3 (FIGS. 2A & 2C), a protein also implicated in mediating spindle check-point response (6,8,9). The structural relatedness between yeast Bub1 and yeast MAD3 has been reported (9). In addition, hBub1 protein appears to contain a domain (152 amino acid residues) homologous to the tail domain of murine kinesin-like protein (muKIF4, ref. 23) with a 22% residue identity (FIGS. 2B & 2C).

Figure 3:
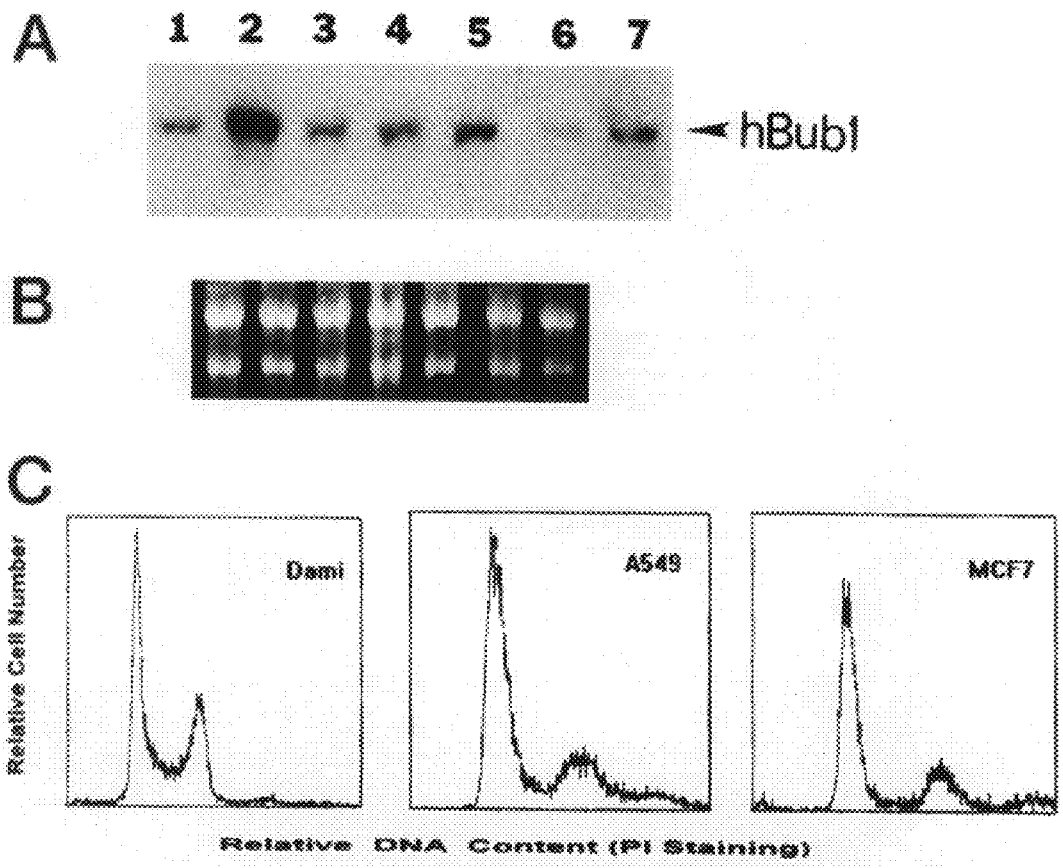
FIGS. 3A, 3B and 3C Analyses of hBub1 mRNA expression in various cell lines. A. Lanes 1 to 7 represent RNA samples from A549, Dami, DU145, GM00637D, K562, MCF-7, and PC-3, respectively. B, Ethidium bromide-stained RNA gel as shown in A as a loading control. C, Flow cytometry analyses of proliferating Dami, A549, and MCF7 cells.
Figure 4:
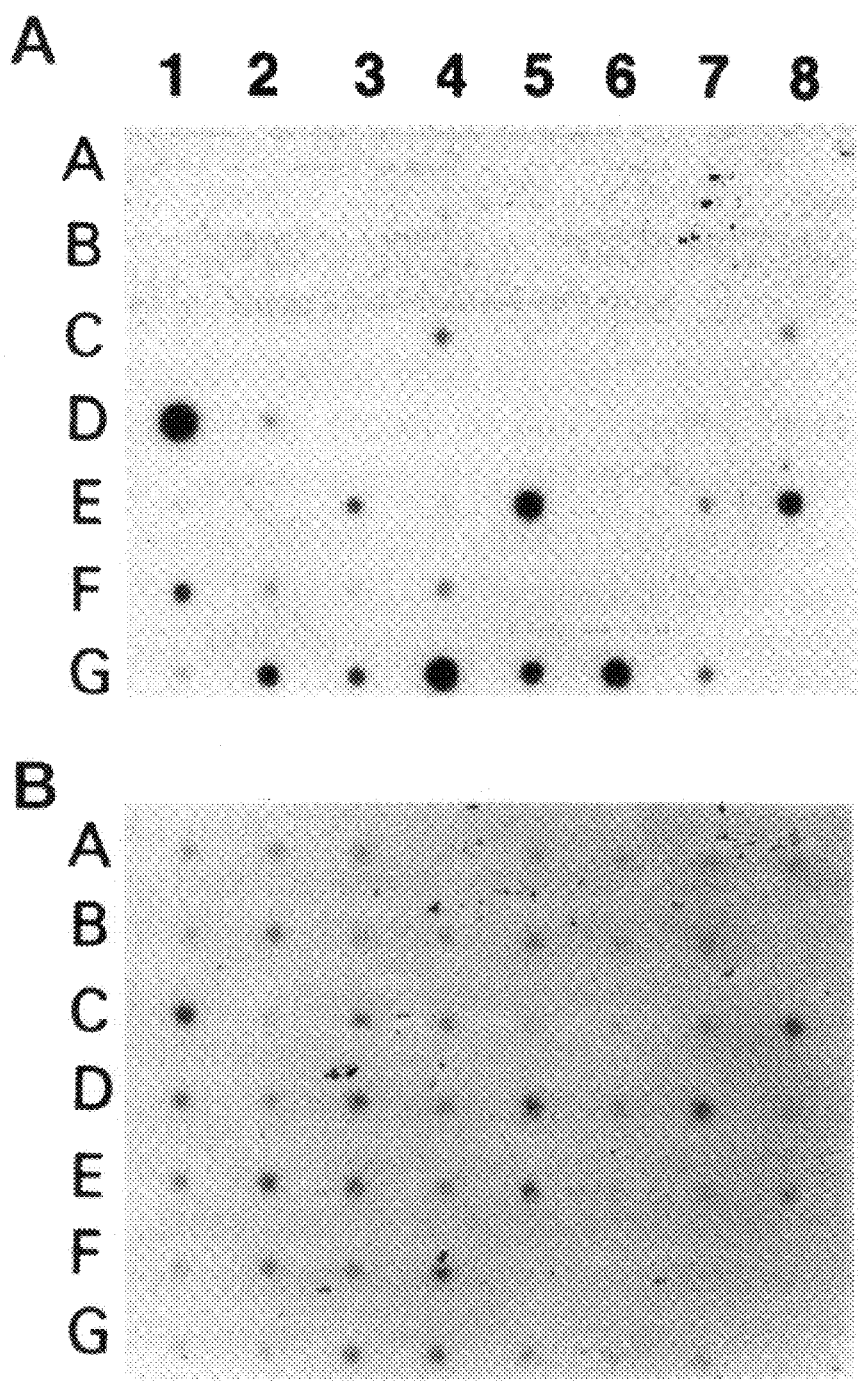
FIGS. 4A and 4B Analysis of hBub1 mRNA expression in primary human tissues. A, A dot blot containing an equal amount of total RNA isolated from fifty primary human tissues was probed for hBub1 expression. B, The same blot was stripped and re-probed with anti-(-actin cDNA. The sample IDs were shown in Table 1.

To elucidate the potential biological role of hBub1, we first examined the pattern of hBub1 mRNA expression in various human tumor cell lines. Northern blotting showed the existence of a single species of hBub1-specific mRNA, which is about 3.5 kbp (FIG. 3A). Although varying among different cell lines, hBub1 mRNA expression was rather ubiquitous. Among twelve cell lines examined (seven shown), Dami, a megakaryoblastic leukemia cell line, expressed the highest level of hBub1 mRNA (FIG. 3A, lane 2). MCF-7, on the other hand, contained a lower level of steady-state hBub1 mRNA (FIG. 3A, lane 6). Flow cytometric analysis of propidium iodide (PI)-stained cells revealed (FIG. 3C) that Dami cell line had a higher mitotic index than A549 and MCF-7 cells. There were about 40% cycling cells in S, G2, and M phases in Dami as compared to 29% in A549 and 25% in MCF-7 cells (data not shown). Furthermore, a survey of fifty primary human tissues for hBub1 expression indicated that various fetal tissues, bone marrow, and thymus, expressed a moderate-to-high level of hBub1 transcripts (FIG. 3C & Table 1). On the other hand, differentiated tissues, such as various brain tissues, muscle, and heart, expressed little-or-no detectable level of hBub1 transcripts (FIG. 4A & Table 1). The multiple tissue blot was also probed with a control gene probe. We confirmed that a roughly equal amount of RNA from various tissues was loaded on to the blot (FIG. 4B). The summarized hBub1 mRNA expression results are shown in Table 1.

TABLE 1

Summary of hBub1 Expression in Fifty Primary Human Tissue

|  | Sample ID | Relative Levels (arbitrary unit) |
|---|---|---|
| Tissue Line |  |  |
| Whole brain | A1 | ND |
| Amygdala | A2 | ND |
| Caudate Nucleus | A3 | ND |
| Cerebellum | A4 | ND |
| Cerebral cortex | A5 | ND |
| Frontal lobe | A6 | ND |
| Hippocampus | A7 | ND |

TABLE 1-continued

Summary of hBub1 Expression in Fifty Primary Human Tissue

| | Sample ID | Relative Levels (arbitrary unit) |
|---|---|---|
| Medulla oblogata | A8 | ND |
| Occipital lobe | B1 | ND |
| Putamen | B2 | ND |
| Subtantia nigra | B3 | ND |
| Temporal lobe | B4 | ND |
| Thalamus | B5 | ND |
| Subthalamic nucleus | B6 | 1 |
| Spinal cord | B7 | ND |
| Heart | C1 | 1 |
| Aorta | C2 | 1 |
| Skeletal muscle | C3 | ND |
| Colon | C4 | 5 |
| Bladder | C5 | ND |
| Uterus | C6 | 1 |
| Prostate | C7 | 1 |
| Stomach | C8 | 4 |
| Testis | D1 | 94 |
| Ovary | D2 | 3 |
| Tissue Type | | |
| Pancreas | D3 | ND |
| Pituitary gland | D4 | ND |
| Adrenal gland | D5 | 1 |
| Thyroid gland | D6 | 1 |
| Salivary gland | D7 | 2 |
| Mammary gland | D8 | 1 |
| Kidney | E1 | 2 |
| Liver | E2 | 1 |
| Small intestine | E3 | 7 |
| Spleen | E4 | 3 |
| Thymus | E5 | 41 |
| Peripheral leukocyte | E6 | ND |
| Lymph node | E7 | 4 |
| Bone marrow | E8 | 21 |
| Tonsil | F1 | 9 |
| Lung | F2 | 3 |
| Trachea | F3 | 2 |
| Placenta | F4 | 4 |
| Fetal brain | G1 | 3 |
| Fetal heart | G2 | 17 |
| Fetal kidney | G3 | 8 |
| Fetal liver | G4 | 69 |
| Fetal spleen | G5 | 20 |
| Fetal thymus | G6 | 43 |
| Fetal lung | G7 | 6 |

A human RNA master blot purchased from Clontech was hybridized with a hBub1 cDNA probe labeled with $^{32}P$. The hBub1-specific signals detected were quantified with a densitometer; ND: non-detectable.

Figure 5:
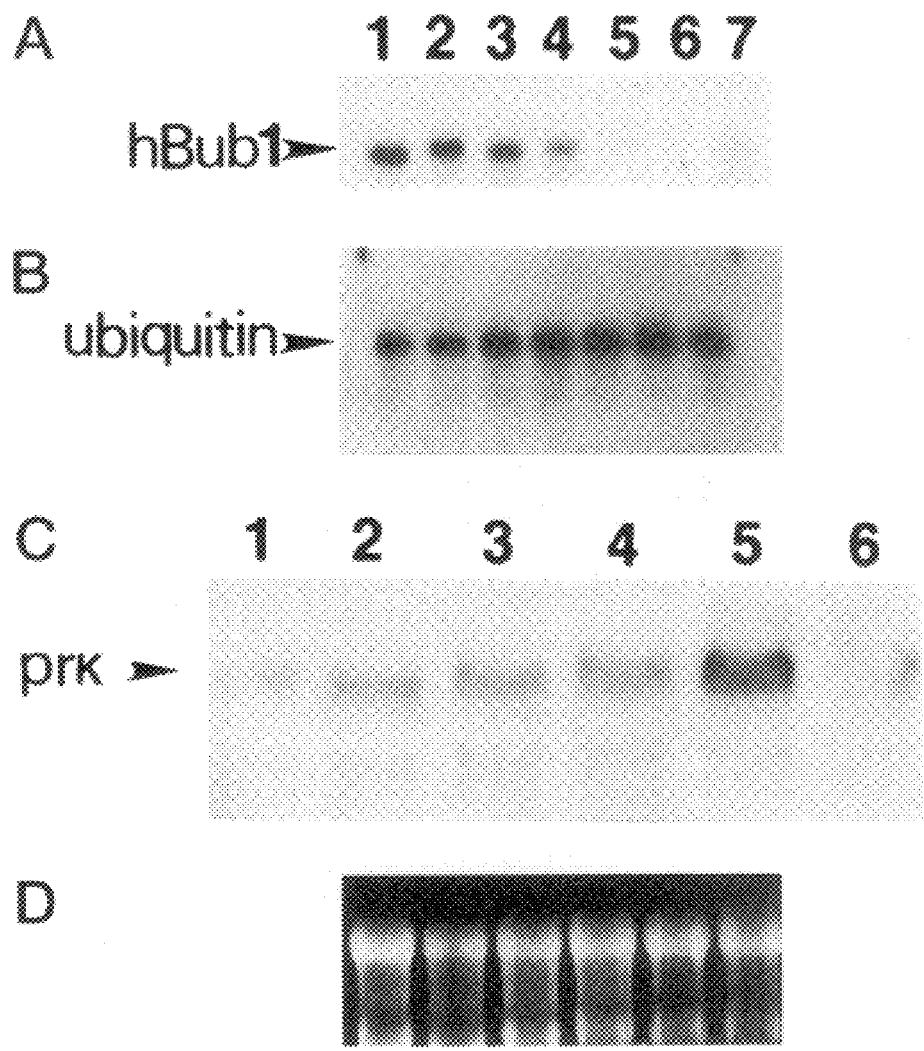
FIGS. 5A, 5B, 5C and 5D hBub1 expression in differentiating Dami cells. Dami cells were treated with PMA for 1 (lane 2), 2 (lane 3), 4 (lane 4), 8 (lane 5), 12 (lane 6) and 24 (lane 7) hours or with the vehicle (lane 1). Equal amounts of total RNA isolated from the treated cells were analyzed for hBub1 (A), ubiquitin (B), or prk expression (C & D) via Northern blotting.

Because Dami cells express a significant level of hBub1 mRNA and because these cells can be induced to differentiate towards more mature megakaryocytes when they are treated with phobol esters (24), this cell line was used to study hBub1 expression during differentiation. Dami cells treated with PMA or vehicle (ethanol) for various time were collected. Total RNA isolated from control and treated cells were analyzed for hBub1 mRNA levels via Northern blotting. FIG. 5A shows that hBub1 expression was rapidly downregulated when cells were exposed to PMA. By 8 hours post-treatment, little hBub1 mRNA expression was detected (lane 5). The same set of samples were analyzed for ubiquitin expression via Northern blotting. The result was shown in FIG. 5B. We also analyzed expression of prk, a polo family cell-cycle kinase gene (25,26) and found that Prk mRNA level was increased by PMA (FIGS. 5C & 5D) although it had almost returned to the pre-treatment level by 24 hours post-treatment (lane 6).

Figure 6:
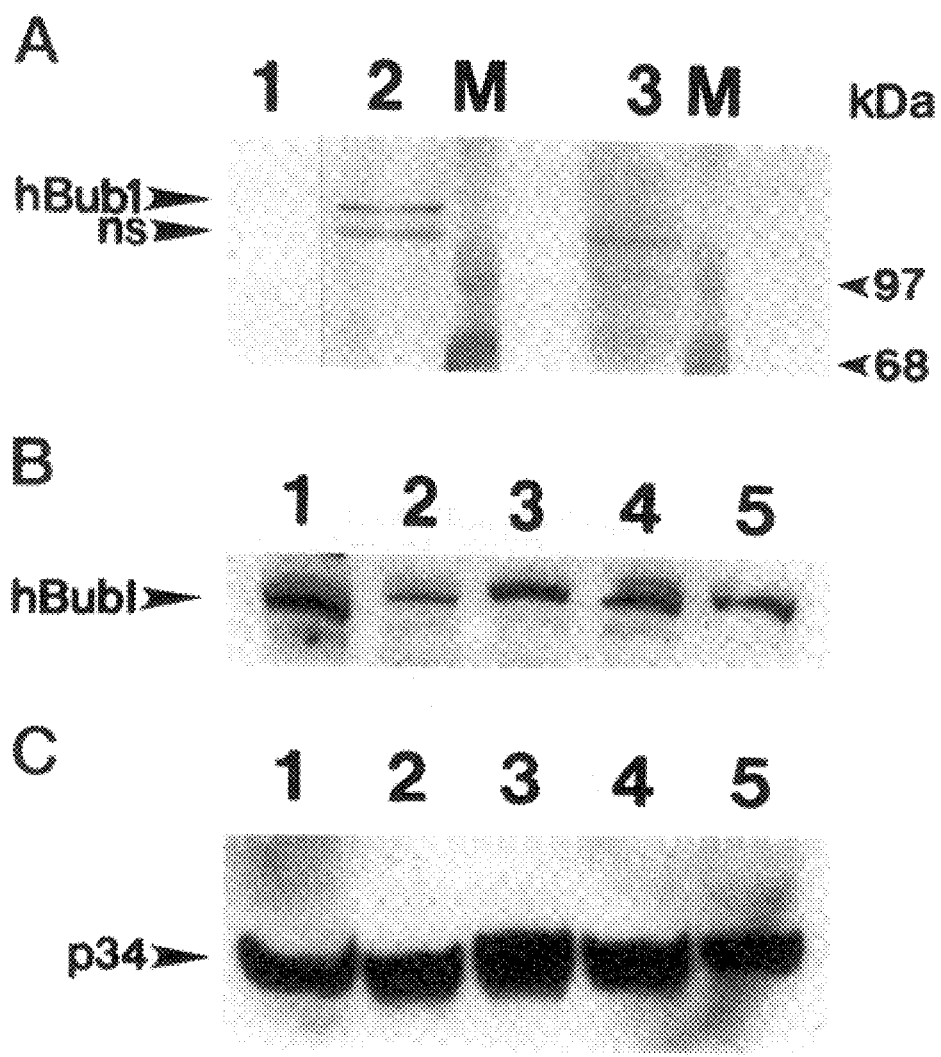
FIGS. 6A, 6B and 6C hBub1 protein levels during the cell cycle. A, Protein blots containing A549 cell lysates were probed with a normal rabbit serum (lane 1) or the anti-hBub1 antiserum in the presence (lane 3) or absence (lane 2) of a molar excess amount of hBub1 peptide. The arrow "ns" indicates a non-competitive antigen. B, A549 cells synchronized at various stages of the cell cycle were analyzed for hBub1 antigen levels via Western blotting. Lane 1, asynchronized; lane 2, G1; lane 3, G1/S; lane 4, late S and G2; lane 5, M. C, The blot as shown in B was stripped and re-probed for p34cdc2 antigen level.

Yeast BUB1 was initially identified as a spindle checkpoint gene (6,9). In order to determine whether the hBub1 protein level was modulated during the cell cycle, polyclonal anti-peptide antisera were raised in rabbits. The anti-serum from rabbit #495 (FIG. 6A, lane 2), but not the normal rabbit serum (lane 1), detected two antigens of about 115 kDa and 122 kDa, respectively, as shown on the Western blot. The 122 kDa signal was absent when the antiserum was pre-absorbed with hBub1 peptide used as an immunogen (FIG. 6A, lane 3), indicating that the 122-kDa band was hBub1. To determine hBub1 protein levels during the various stages of the cell cycle, A549 cells were synchronized as described in Experimental Procedures, and equal amounts of protein lysates were analyzed for hBub1 levels via Western blotting. FIG. 6B shows that hBub1 protein level was low in G1 (about 35% of S/G2 or M phase level as determined by densitometry) and remained relatively constant during the rest of the cell cycle. The same blot was also probed with anti-p34cdc2 antibody and the results are shown in FIG. 6C.

Figure 7:
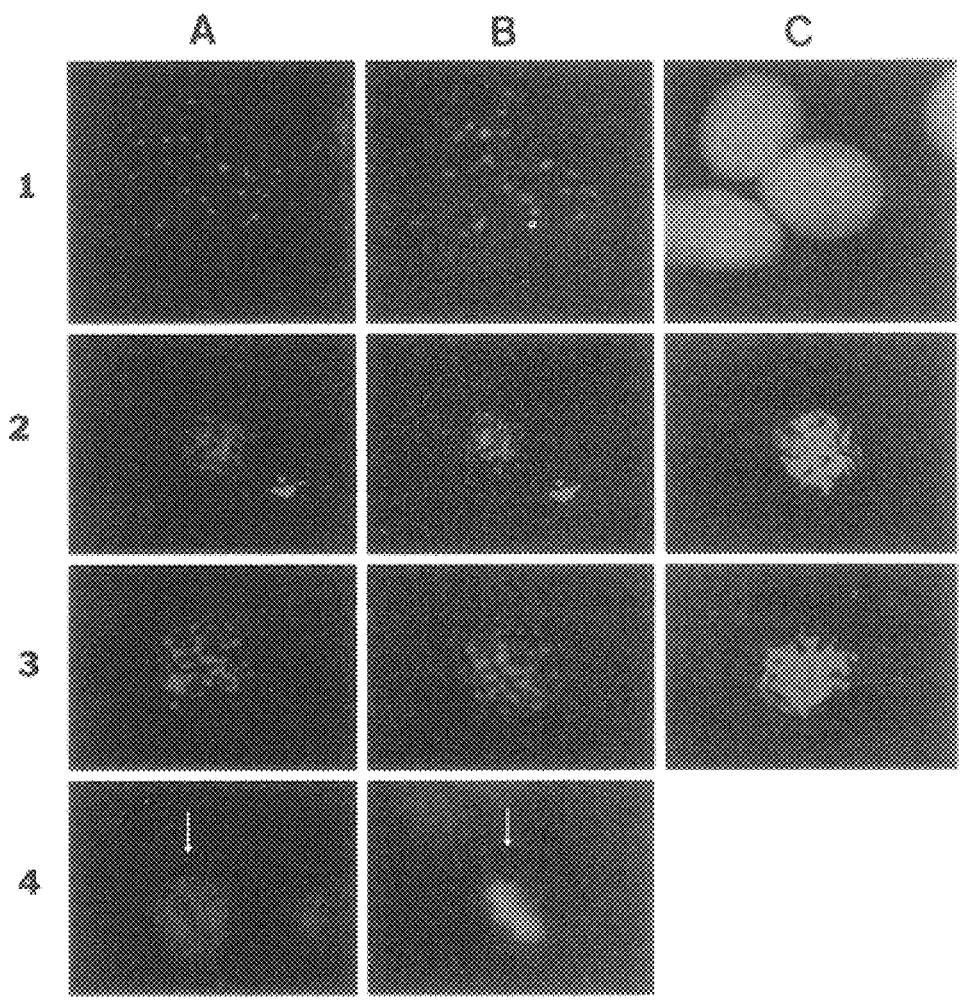
FIG. 7. Subcellular localization of hBub1 in PC-3 cells. PC-3 cells were stained with the anti-hBub1 antiserum (column 1) or an antiserum (CREST) to kinetochore (column 2 except for row 4). DNA was visualized with DAPI (column 3). Row 1, interphase cells; Row 2, prophase cell; Row 3, cell treated with nocodazole for 18 hours. Row 4, metaphase cell (hBub1 staining is in green and DNA staining is in column 2).

To determine the subcellular localization of hBub1, we used the anti-hBub1 antibody to stain the protein in proliferating A549 cells. In interphase cells, significant hBub1 staining was detected in nucleus co-localizing with the kinetochore antigen CREST (FIG. 7, row 1). In mitotic prophase cells, hBub1 staining remains associated with condensed chromosomes and co-localizes with CREST antigen (FIG. 7, row 2). However, when cells enter metaphase, hBub1 antigen was no longer associated with the chromosomes exhibiting a diffused pattern around mitotic spindles (FIG. 7, row 4). On the other hand, when A549 cells were treated with nocodazole, a spindle-assembly disrupting agent, hBub1 staining was co-localized with CREST (FIG. 7, row 3), suggesting a role of hBub1 in monitoring the integrity of spindle-kinetochore interaction.

To further determine whether hBub1 is involved in the spindle checkpoint pathway, we introduced affinity-purified anti-hBub1 antibody into A549 cells through electroporation and examined their response to spindle assembly inhibitor nocodazole as described (13). We observed that the mitotic index (the percentage of electroporated cells in mitosis) of cells electroporated with anti-hBub1 antibody was consistently lower than the cells electroporated with pre-immune IgG. This suggests that hBub1 is important in A549 cells for full execution of the spindle checkpoint.

Figure 8:
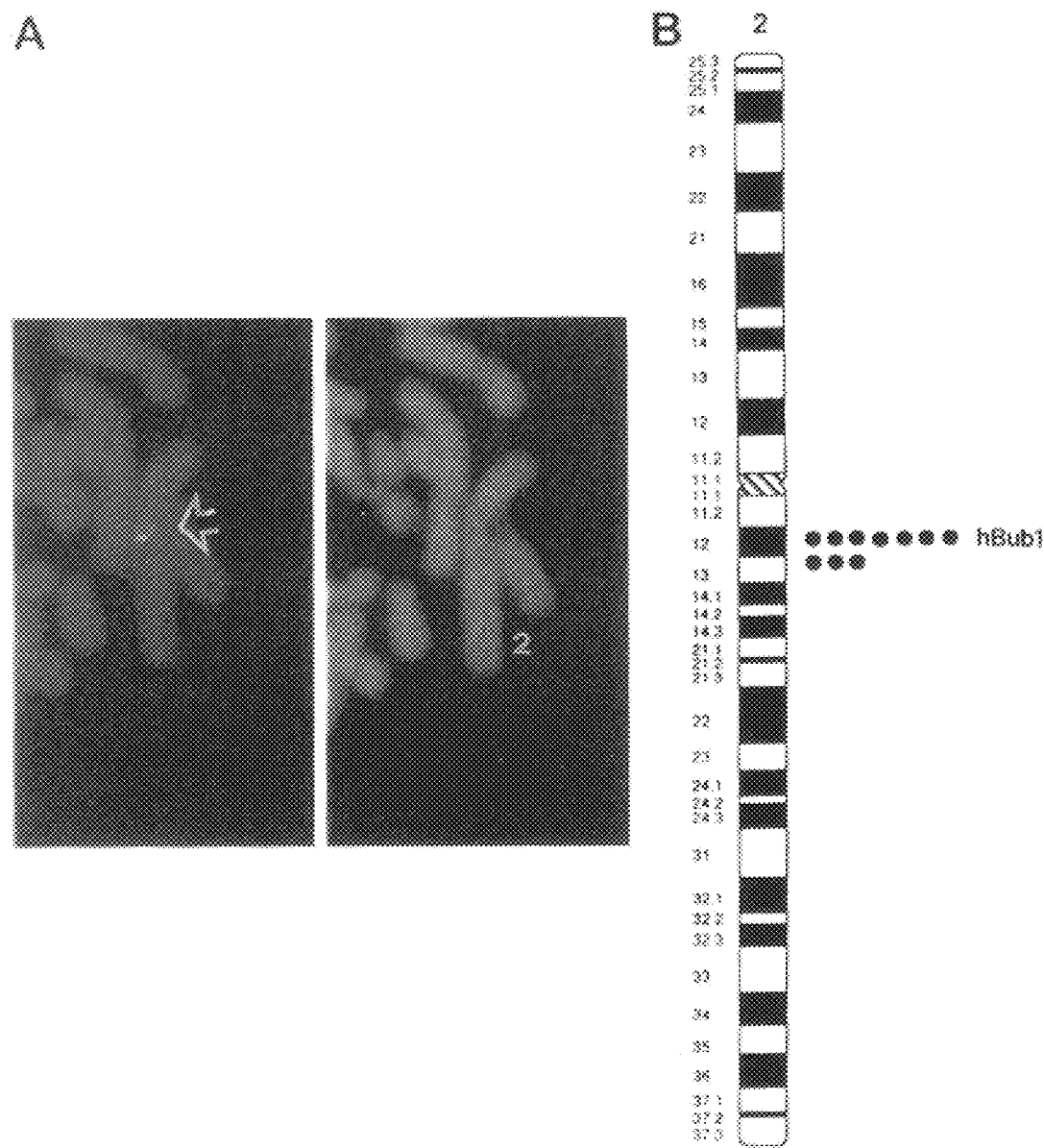
FIGS. 8A and 8B Chromosomal mapping of hBub1 gene. The chromosome localization of hBub1 gene was achieved by in situ hybridization with fluorescently labeled hBub1 cDNA. Arrow indicates hBub1 gene localization at 2q12–13.
Figure 8B:
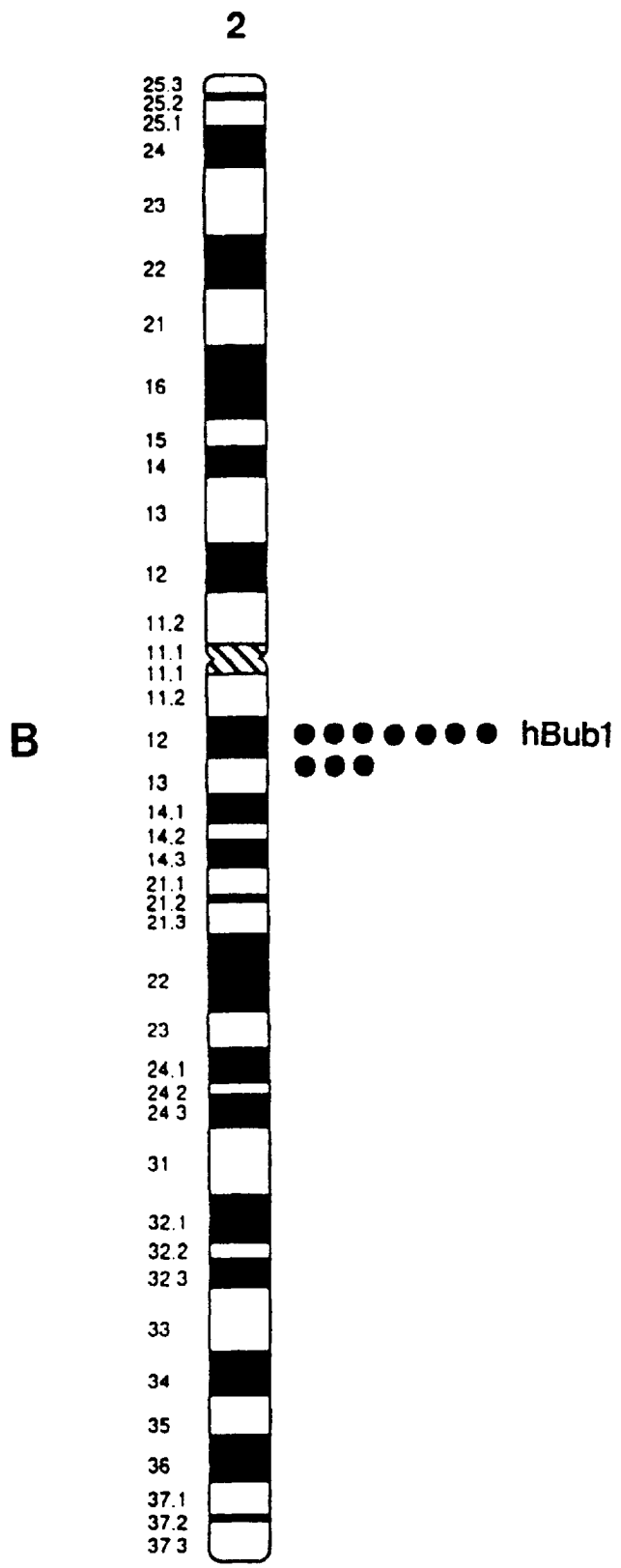

Structural abnormalities of many genes, such as p53 and ATM involved in checkpoint controls, contribute significantly to malignant transformation of multi-cellular organisms (27,28). To gain an insight into whether hBub1 gene might be linked to certain genetic diseases such as cancer, FISH and DAPI banding analyses were employed for mapping the hBub1 gene. It was shown that signals were detected on human chromosome 2q12–13 (FIGS. 8A & 8B). Consistent signals were not detected in other chromosomal regions under conditions used, nor did the control probe show any signals under the same conditions.

EXAMPLES

Example 1

Two Step Assay to Detect the Presence of hBub1 in a Sample

Patient sample is processed according to the method disclosed by Antonarakis et al. (1985), separated through a 1% agarose gel and transferred to nylon membrane for Southern blot analysis.

Membranes are UV cross linked at 150 mJ. hBub1 probe corresponding to nucleotide positions 406 to 1272 of AF043294 for 10 min at room temperature with 1×SSC.

Blots are incubated for 10 min at room temperature with shaking in the substrate buffer consisting of 0.1M diethanolamine, 1 mM MgCl2, 0.02% sodium azide, pH 10.0. Individual blots are placed in heat sealable bags with substrate buffer and 0.2 mM AMPPD (3-(2'-spiroadamantane)-4-methoxy-4-(3'-phosphoryloxy)phenyl-1,2-dioxetane, disodium salt, Bio-Rad). After a 20 min incubation at room temperature with shaking, the excess AMPPD solution is removed. The blot is exposed to X-ray film overnight. Positive bands indicate the presence of hBub1.

Example 2
Generation of Polyclonal Antibody against hBub1

Segments of hBub1 coding sequence are expressed as fusion protein in *E. coli*. The overexpressed protein are purified by gel elution and are used to immunize rabbits and mice using a procedure similar to the one described by Harlow and Lane, 1988. This procedure has been shown to generate Abs against various other proteins (for example, see Kraemer et al., 1993).

Briefly, a stretch of hBub1 coding sequence is cloned as a fusion protein in plasmid. The hBub1 incorporated sequence includes the amino acids corresponding to SEQ ID NO:2. After induction, the overexpression of a fusion protein with the expected molecular weight is verified by SDS/PAGE. Fusion protein is purified from the gel by electroelution. The identification of the protein as the hBub1 fusion product is verified by protein sequencing at the N-terminus. Next, the purified antibody containing serum is collected two weeks thereafter.

This procedure is repeated to generate antibodies against the mutant forms of the hBub1 gene. These antibodies, in conjunction with antibodies to wild type hBub1, are used to detect the presence and the relative level of the mutant forms in various tissues and biological fluids.

Example 3
Generation of Monoclonal Antibodies Specific for hBub1

Monoclonal antibodies are generated according to the following protocol. Mice are immunized with injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, myeloma are fused with immune spleen cells using polyethylene glycol as described by Harlow and Lane, 1988. Cells are plated at a density of about 2×105 cells/well in 96 well tissue culture plates. Individual wells are examined for growth and the supernatants of wells with growth are tested for the presence of hBub1 specific antibodies by ELISA or RIA using wild type or mutant hBub1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 4
Sandwich Assay for hBub1

Monoclonal antibody is attached to a solid surface such as a plate, tube, bead, or particle. Preferably, the antibody is attached to the well surface of a 96-well ELISA plate. 100 or a chromophore) and the solid phase with the second antibody is incubated for two hrs at room temperature. The second antibody is decanted and the solid phase is washed with buffer to remove unbound material.

The amount of bound label, which is proportional to the amount of hBub1 peptide/protein present in the sample, is quantitated. Separate assays are performed using monoclonal antibodies that are specific for the wild-type hBub1 as well as monoclonal antibodies specific for each of the mutations identified in hBub1.

Example 5
Detecting hBub1 Mutations and Deletions

Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

REFERENCES

1. Weinert, T. (1997) A DNA damage checkpoint meets the cell cycle engine. Science 277, 1450–1451.
2. Nasmyth, K. (1996) Viewpoint: putting the cell cycle in order. Science 274, 1643–1645.
3. Pines, P. (1994) The cell cycle kinases. Seminar in Cancer Biol. 15, 305–313.
4. Elledge, S. J. (1996) Cell cycle checkpoints: preventing an identity crisis. Science 274, 1664–1672.
5. Paulovich, A. G., Toczyski, P. P., and Hartwell, L. H. (1997) When checkpoints fail. Cell 88, 315–321.
6. Hoyt, M. A., Totis, L., and Roberts, B. T. (1991) *S. cerevisiae* genes required for cell cycle arrest in response to loss of microtubule function. Cell 66, 507–517.
7. Li, R., and Murray A. W. (1991) Feedback control of mitosis in budding yeast. Cell 66, 519–531.
8. Hardwick K. G. (1998) The spindle checkpoint. Trend in Genetics.
9. Roberts, B. T., Farr, K. A., and Hoyt, M. A. (1994) The *Sacchromyces cerevisiae* checkpoint BUB1 encodes a novel protein kinase. Mol. Cell. Biol. 14, 8282–8291.
10. Farr, K., Hoyt, M. A. (1998) Bub1p kinase activates the *Saccharomyces cerevisiae* spindle assembly checkpoint. Mol. Cell. Biol. 18, 2738–2747.
11. Fankhauser, C., Mark, J., Reymond, A., and Simanis, V. (1993) The *S. pombe* cdc16 gene is required both for 12. Hardwick, K., and Murray, A. W. (1995) Mad1p, a phosphoprotein component of the spindle assembly checkpoint in budding yeast. J. Cell Biol 131, 709–720.
13. Li, Y., and Benezra, R. (1996) Identification of a human mitotic checkpoint gene: hsMAD2. Science 274, 246–248.
14. Chen, R. H., Waters, J. C., Salmon, E. D., and Murray, A. W. (1996) Association of spindle checkpoint component XMAD2 with unattached kinetochore. Science 274, 242–245.
15. Taylor, S. S., and McKeon, F. (1997) Kinetochore localization of murine Bub1 is required for normal mitotic timing and checkpoint response to spindle damage. Cell 89, 727–735.
16. Gahill, D. P., Lengauer, C., Yu, J., Riggins, G. J., Willson, J. K. V., Markowitz, S. D., Kinzler, K. W., Vogelstein, B. (1998) Mutations of mitotic checkpoint genes in human cancers. Nature 392, 300–303.
17. Duesbery, N. S., Choi, T., Brown, K., Wood, K. W., Resau, J., Fukasawa, K., Cleveland, D. W., Vande Woude, G. F. (1997) CENP-E is an essential kinetochore motor in maturing oocytes and is masked during Mos-dependent, cell cycle arrest at metaphase II. Proc. Natl. Acad. Sci. USA 94.
18. Heng, H. H. Q., Squire, J., Tsui, L. (1992) High resolution mapping of mammalian genes by in situ hybridization to free chromatin. Proc. Nati. Acad. Sci. USA 89, 9509–9513.
19. Heng H. H. Q., and Tsui, L. (1993) Models of DAPI banding and simultaneous in situ hybridization. Chromosoma 102, 325–332.
20. Hermeking, H., Lengauer, C., Polyak, K., He, T. C., Zhang, L., Thiagalingam, S., Kinzler, K. W., and Vogelstein, B. (1997) 14-3-3(is a p53-regulated inhibitor of G2/M progression. Mol. Cell 1,3–11.
21. Kozak, M. (1984) Compilation and analysis of sequences upstream from the translational start site in eukaryotic mRNAs. Nucd. Acids Res. 12, 857–872.
22. Hanks, S. K., Quinn, A. M., and Hunter, T. (1988) The protein kinase family: conserved features and deduced phylogeny of the catalytic domains. Science 241, 42–52.
23. Sekline, Y., Okada, Y., Noda, Y., Kondo, S., Aizawa, H., Takemura, R., and Hirokawa, N. (1994). A novel microtubule-based motor protein (KIF4) for organelle transports, whose expression is regulated developmentally. J. Cell Biol. 127, 187–201.
24. Greenberg, S. M., Rosenthal, D. S., Tantravahi, R., and Handin, R. I. (1988) Characterization of a new megakaryocytic cell line: the Dami cell. Blood 72, 1968–1977.
25. Ouyang, B., Pan, H., Lu L., Stambrook, P., Li, B., and Dai W. (1997) Human Prk is a conserved protein serine/threonine kinase involved in regulating M phase function. J Biol Chem 272, 28646–28651.
26. Li, B., Ouyang, B., Pan, H., Reissmann, P., Slamon, D. J., Arceci, R., Luo, L., and Dai W. (1996) prk, a cytokine-inducible human protein serine/threonine kinase whose expression appears to be down-regulated in lung carcinoma. J. Biol. Chem. 271, 19402–19408.
27. Sherr, C. J. (1996) Cancer cell cycle. Science 274, 1672–1677.
28. Xu, Y., Ashley, T., Brainerd, E. E., Bronson, R. T., Meyn, M. S., Baltimore, D. (1996) Targeted disruption of ATM leads to growth retardation, chromosomal fragmentation during meiosis, immune defects, and thymic lymphoma. Genes & Develop 10, 2411–2422.
29. Sanchez, Y., Wong, C., Thomas, R. S., Richman,R., Wu. Z., Piwnica-Worms, H., and Elledge, S. J. (1997) Conservation of the chk1 checkpoint pathway in mammals: linkage of DNA damage to Cdk regulation through Cdc25. Science 277, 1497–1051.

While the preferred embodiment of the invention has been illustrated and described, it is to be understood that, within the scope of the appended claims, various changes can be made therein. Hence, the invention can be practiced in ways other than those specifically described herein.

We claim:

1. An isolated nucleic acid molecule consisting of the sequence shown in SEQ ID NO. 1.

2. The isolated nucleic acid molecule of claim 1, wherein the nucleic acid molecule is a DNA molecule.

3. The isolated nucleic acid molecule of claim 2, wherein the DNA molecule is a cDNA molecule.

4. A recombinant expression vector comprising the isolated nucleic acid molecule of claim 3 operably linked to a promoter sequence which directs transcription of said nucleic acid molecule in a cell transfected or transduced with said recombinant expression vector.

5. The vector of claim 4, wherein the vector is a plasmid.

6. The vector of claim 4, wherein the vector is a virus.

7. A host vector system that further comprises the vector of claim 4 in a suitable isolated host cell.

8. The host vector system of claim 7, wherein the host cell is a bacterial cell.

9. The host vector system of claim 7, wherein the host cell is a eucaryotic cell.

10. The host vector system of claim 9, wherein the eucaryotic cell is a mammalian cell.

11. A method for producing a protein which comprises growing the host vector system of claim 9 under conditions permitting the production of the protein and recovering the protein produced thereby.

12. The isolated nucleic acid molecule of claim 1, wherein the nucleic acid molecule is an RNA molecule.

13. A method for detecting the presence of hBub1 nucleic acid in a biological sample, comprising:
   a) selecting a probe from SEQ ID NO. 1 that specifically hybridizes to hBub1;
   b) hybridizing the probe with the biological sample;
   c) detecting the presence of a hybridization complex formed by the hybridization of the probe with the hBub1 nucleic acid sample, wherein the presence of the complex is indicative of the presence of hBub1 nucleic acid in the sample.

14. The method of claim 13 wherein the probe is DNA.

15. The method of claim 13 wherein the probe is RNA.

16. The method of claim 14 wherein the probe contains a homozygous deletion.

17. The method of claim 13 wherein the probe is detectably labeled.

18. The method of claim 17 wherein the label is selected from the group consisting of a radioisotope, a bioluminescent compound, a chemiluminescent compound, a fluorescent compound, a metal chelate and an enzyme.

19. A diagnostic kit useful for the detection of a deletion mutation in hBub1 nucleic acid, said kit comprising a container including a probe for detection of a deletion mutation in the hBub1 nucleic acid and a pharmaceutically acceptable carrier, wherein said probe is selected from the group consisting of:
   a) a nucleic acid molecule consisting of the sequence shown in SEQ ID NO. 1, wherein T can also be U;
   b) a nucleic acid molecule consisting of the sequence shown in SEQ ID NO. 1;
   c) a nucleic acid molecule fully complementary to (a);
   d) a nucleic acid molecule fully complementary to (b); and combinations thereof.

20. The kit of claim 19 wherein the probe is a hybridization probe.

21. A method for screening a gemniline of a human subject for an alteration of hBub1 gene, which comprises comparing a germline sequence of an hBub1 gene or hBub1 RNA from a tissue sample from said subject, or a sequence of hBub1 cDNA made from mRNA from said sample, with the germline sequences of wild-type hBub1 gene, wild-type hBub1 RNA, or wild-type hBub1 cDNA, wherein a difference in the sequence of the hBub1 gene, hBub1 RNA or hBub1 cDNA of the subject from the wild-type indicates alteration in the hBub1 gene in said subject and wherein the wild-type hBub1 gene has the sequence set forth in SEQ ID NO: 1.

22. The method of claim 21 wherein the nucleic acid sequence of hBub1 RNA from the subject is compared to nucleic acid sequences of wild-type hBub1 gene, hBub1 RNA or hBub1 cDNA.

23. The method of claim 22 wherein the nucleic acid sequence is compared by hybridizing an hBub1 gene probe which specifically hybridizes to a hBub1 allele, to RNA isolated from said subject and detecting the presence of a hybridization product, wherein the presence of said product indicates the presence of said allele in said subject.

24. The method of claim 21 wherein a regulatory region of the hBub1gene from said subject is compared with a regulatory region of wild-type hBub1gene sequences.

25. The method of claim 21 wherein the germline nucleic acid sequence is compared by hybridizing an hBub1 gene probe which specifically hybridizes to an hBub1 allele, to genomic DNA isolated from said sample and detecting the presence of a hybridization product, wherein the presence of said product indicates the presence of said allele in said subject.

26. The method of claim 21 wherein the germline nucleic acid sequence is compared by amplifying all or part of an hBub1 gene from said sample using a set of primers to produce amplified nucleic acids and sequencing said amplified nucleic acids.

27. The method of claim 21 wherein the gelmine nucleic acid sequence is compared by amplifying all or part of an hBub1 gene using a primer specific for a specific hBub1 mutant allele and detecting the presence of an amplified product, wherein the presence of said product indicates the presence of said specific allele.

28. The method of claim 21 wherein the germline nucleic acid sequence is compared by molecularly cloning all or part of a hBub1 gene from said sample to produce a cloned nucleic acid and sequencing said cloned nucleic acid.

29. The method of claim 21 wherein the germline nucleic acid sequence is compared by analyzing hBub1 nucleic acids in said sample for a deletion mutation.

30. The method of claim 21 wherein the germline nucleic acid sequence is compared by analyzing hBub1 nucleic acids in said sample for a point mutation.

31. The method of claim 21 wherein the germline nucleic acid sequence is compared by analyzing hBub1 nucleic acids in said sample for an insertion mutation.

* * * * *

UNITED STATES PATENT AND TRADEMARK OFFICE
CERTIFICATE OF CORRECTION

PATENT NO.    : 6,335,169 B1                                                    Page 1 of 1
DATED         : January 1, 2002
INVENTOR(S)   : Wei Dai, Bin Ouyang, Huiqi Pan and Zhengdao Lan It is certified that error appears in the above-identified patent and that said Letters Patent is hereby corrected as shown below:

<u>Column 3,</u>
Line 23, "FIGS. 2A, 2B and 2B" should read -- FIGS. 2A, 2B and 2C --

<u>Column 1,</u>
Line 8, "grant RO1CA74299 awarded" should read -- grant RO1CA74229 awarded --

Signed and Sealed this

Fourth Day of June, 2002

*Attest:*

*Attesting Officer*

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 3332
<212> TYPE: DNA
<213> ORGANISM: Homo sapiens; Eukaryota; Animalia; Metazoa; Chordata;
      Vertebrata;Mammalia;
<220> FEATURE:

<400> SEQUENCE: 1

```
ggtttgccgc tgccgcccag cgtcttttgg ccatggacac cccggaaaat gtccttcaga      60
tgcttgaagc ccacatgcaa gagtacaagg gcaatgacct tcttggtgaa tgggaaagat     120
acatacagtg ggtagaagag aattttcctg agaataaaga atacttgata actttactag     180
aacatttaat gaaggaattt ttagataaga agaaatacca caatgaccca agattcatca     240
gttattgttt aaaatttgct gagtacaaca gtgacctcca tcaattttt gagtttctgt     300 acaaccatgg gattggaacc ctgtcatccc ctctgtacat tgcctgggcg gggcatctgg     360
aagcccaagg agagctgcag catgccagtg ctgtccttca gagaggaatt caaaaccagg     420
ctgaacccag agagttcctg caacaacaat acaggttatt tcagacacgc ctcactgaaa     480
```

-continued

```
cccatttgcc agctcaagct agaacctcag aacctctgca taatgttcag gttttaaatc    540
aaatgataac atcaaaatca aatccaggaa ataacatggc ctgcatttct aagaatcagg    600
gttcagagct ttctggagtg atatcttcag cttgtgataa agagtcaaat atggaacgaa    660
gagtgatcac gatttctaaa tcagaatatt ctgtgcactc atctttggca tccaaagttg    720
atgttgagca ggttgttatg tattgcaagg agaagcttat tcgtggggaa tcagaatttt    780
cctttgaaga attgagagcc cagaaataca atcaacggag aaagcatgag caatgggtaa    840
atgtagacac acattatatg aaaaggaaag aagcaaatgc ttttgaagaa cagctattaa    900
aacagaaaat ggatgaactt cataagaagt tgcatcaggt ggtggagaca tcccatgagg    960
atctgcccgc ttcccaggaa aggtccgagg ttaatccagc acgtatgggg ccaagtgtag    1020
gctcccagca ggaactgaga gcgccatgtc ttccagtaac ctatcagcgg acaccagtga    1080
acatggaaaa gaacccaaga gaggcacctc ctgttgttcc tcctttggca aatgctattt    1140
ctgcagcttt ggtgtcccca gccaccagcc agagcactgc tcctcctgtt cctttgaaag    1200
cccagacagt aacagactcc atgtatgcag tggccagcaa agatgctgga tgtgtgaata    1260
agagtactca tgaattcaag ccacagagtg gagcagagat caaagaaggg tgtgaaacac    1320
ataaggttgc caacacaagt tcttttcaca caactccaaa cacatcactg ggaatggttc    1380
agtcaacgcc atccaaagtg cagccatcac ccaccgtgca cacaaaagaa gcattaggtt    1440
tcatcatgaa tatgtttcag gctcctacac ttcctgatat ttctgatgac aaagatgaat    1500
ggcaatctct agatcaaaat gaagatgcat ttgaagccca gtttcaaaaa aatgtaaggt    1560 catctgggc ttggggagtc aataagatca tctcttcttt gtcatctgct tttcatgtgt    1620
ttgaagatgg aaacaaagaa aattatggat taccacagcc taaaaataaa cccacaggag    1680
ccaggaccct tggagaacgc tctgtcagca gacttccttc aaaaccaaag gaggaagtgc    1740
ctcatgctga agagttttg gatgactcaa ctgtatgggg tattcgctgc aacaaaaccc    1800
tggcacccag tcctaagagc ccaggagact tcacatctgc tgcacaactt cgtctacac    1860 cattccacaa gcttccagtg gagtcagtgc acatttaga agataaagaa aatgtggtag    1920
caaaacagtg tacccaggcg actttggatt cttgtgagga aaacatggtg gtgctttcaa    1980
gggatggaaa attcagtcca attcaagaga aagcccaaa acaggccttg tcgtctcaca    2040
tgtattcagc atccttactt cgtctgagcc agcctgctgc aggtggggta cttacctgtg    2100
aggcagagtt gggcgttgag gcttgcagac tcacagacac tgacgctgcc attgcagaag    2160
atccaccaga tgctattgct gggctccaag cagaatggat gcagatgagt tcacttggga    2220
ctgttgatgc tccaaacttc attgttggga acccatggga tgataagctg attttcaaac    2280 tttatctgg gctttctaaa ccagtgagtt cctatccaaa tacttttgaa tggcaatgta    2340
aacttccagc catcaagccc aagactgaat ttcaattggg ttctaagctg gtctatgtcc    2400
atcaccttct tggagaagga gcctttgccc aggtgtacga agctacccag ggagatctga    2460
atgatgctaa aaataaacag aaatttgttt taaaggtcca aaagcctgcc aacccctggg    2520
aattctacat tgggacccag ttgatggaaa gactaaagcc atctatgcag cacatgttta    2580
tgaagttcta ttctgcccac ttattccaga atggcagtgt attagtagga gagctgtaca    2640
gctatggaac attattaaat gccattaacc tttataaaaa tacccctgaa aaagtgatgc    2700
ctcaaggtct tgtcatctct ttcgctatga gaatgcttta catgattgag caagtgcatg    2760
actgtgaaat cattcatgga gacattaagc cagataactt catacttgga aacggatttt    2820
tggaacagga tgatgaagat gatttatctg ctggcttggc actgattgac ctgggtcaga    2880
```

```
gtatagatat gaaacttttt ccaaaaggaa ctatattcac agcaaagtgt gaaacatctg    2940
gttttcagtg tgttgagatg ctcagcaaca aaccatggaa ctaccagatc gattactttg    3000
gggttgctgc aacagtatat tgcatgctct ttggcactta catgaaagtg aaaaatgaag    3060
gaggagagtg taagcctgaa ggtcttttta gaaggcttcc tcatttggat atgtggaatg    3120
aattttttca tgttatgttg aatattccag attgtcatca tcttccatct ttggatttgt    3180
taaggcaaaa gctgaagaaa gtatttcaac aacactatac taacaagatt agggccctac    3240
gtaataggct aattgtactg ctcttagaat gtaagcgttc acgaaaataa aatttggata    3300
tagacagtcc ttaaaaaaaa aaaaaaaaa aa                                   3332
```

<210> SEQ ID NO 2
<211> LENGTH: 77
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: Peptide
<222> LOCATION: 30..106

<400> SEQUENCE: 2

Tyr Ile Gln Trp Val Glu Glu Asn Phe Pro Glu Asn Lys Glu Tyr
                 5                  10                  15

Leu Ile Thr Leu Leu Glu His Leu Met Lys Glu Phe Leu Asp Lys
                20                  25                  30

Lys Lys Tyr His Asn Asp Pro Arg Phe Ile Ser Tyr Cys Leu Lys
                35                  40                  45

Phe Ala Glu Tyr Asn Ser Asp Leu His Gln Phe Phe Glu Phe Leu
                50                  55                  60

Tyr Asn His Gly Ile Gly Thr Leu Ser Ser Pro Leu Tyr Ile Ala
                65                  70                  75

Trp Ala

<210> SEQ ID NO 3
<211> LENGTH: 86
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 84..169

<400> SEQUENCE: 3

Tyr Ile Lys Trp Leu Asn Asn Ala Tyr Pro Gln Gly Gly Asn Ser
                 5                  10                  15

Lys Gln Ser Gly Met Leu Thr Leu Leu Glu Arg Cys Leu Ser His
                20                  25                  30

Leu Lys Asp Leu Glu Arg Tyr Arg Asn Asp Val Arg Phe Leu Lys
                35                  40                  45

Ile Trp Phe Trp Tyr Ile Glu Leu Phe Thr Arg Asn Ser Phe Met
                50                  55                  60

Glu Ser Arg Asp Ile Phe Met Tyr Met Leu Arg Asn Gly Ile Gly
                65                  70                  75

Ser Glu Leu Ala Ser Phe Tyr Glu Glu Phe Thr
                80                  85

<210> SEQ ID NO 4
<211> LENGTH: 85

```
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 107..191

<400> SEQUENCE: 4

Gly His Leu Glu Ala Gln Gly Glu Leu Gln His Ala Ser Ala Val
                 5                  10                  15

Leu Gln Arg Gly Ile Gln Asn Gln Ala Glu Pro Arg Glu Phe Leu
                20                  25                  30

Gln Gln Gln Tyr Arg Leu Phe Gln Thr Arg Leu Thr Glu Thr His
                35                  40                  45

Leu Pro Ala Gln Ala Arg Thr Ser Glu Pro Leu His Asn Val Gln
                50                  55                  60

Val Leu Asn Gln Met Ile Thr Ser Lys Ser Asn Pro Gly Asn Asn
                65                  70                  75

Met Ala Cys Ile Ser Lys Asn Gln Gly Ser
                80                  85

<210> SEQ ID NO 5
<211> LENGTH: 82
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 170..251

<400> SEQUENCE: 5

Asn Leu Leu Ile Gln Lys Glu Lys Phe Gln Tyr Ala Val Lys Ile
                 5                  10                  15

Leu Gln Leu Gly Ile Lys Asn Lys Ala Arg Pro Asn Lys Val Leu
                20                  25                  30

Glu Asp Arg Leu Asn His Leu Leu Arg Glu Leu Gly Glu Asn Asn
                35                  40                  45

Ile Gln Leu Gly Asn Glu Ile Ser Met Asp Ser Leu Glu Ser Thr
                50                  55                  60

Val Leu Gly Lys Thr Arg Ser Glu Phe Val Asn Arg Leu Glu Leu
                65                  70                  75

Ala Asn Gln Asn Gly Thr Ser
                80

<210> SEQ ID NO 6
<211> LENGTH: 78
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 212..289

<400> SEQUENCE: 6

Ile Thr Ile Ser Lys Ser Glu Tyr Ser Val His Ser Ser Leu Ala
                 5                  10                  15

Ser Lys Val Asp Val Glu Gln Val Val Met Tyr Cys Lys Glu Lys
                20                  25                  30

Leu Ile Arg Gly Glu Ser Glu Phe Ser Phe Glu Glu Leu Arg Ala
                35                  40                  45

Gln Lys Tyr Asn Gln Arg Arg Lys His Glu Gln Trp Val Asn Val
```

```
                    50                  55                  60
Asp Arg His Tyr Met Lys Arg Lys Glu Ala Asn Ala Phe Glu Glu
                65                  70                  75

Gln Leu Leu

<210> SEQ ID NO 7
<211> LENGTH: 70
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 880..950

<400> SEQUENCE: 7

Ile Leu Val Ser Lys Leu Glu Ser Ser Leu Asn Gln Ser Lys Ala
                 5                  10                  15

Ser Cys Ile Asp Val Gln Lys Met Leu Phe Glu Glu Gln Asn His
                20                  25                  30

Phe Ala Lys Ile Glu Thr Glu Leu Lys Glu Glu Leu Val Lys Val
                35                  40                  45

Glu Gln Gln His Gln Glu Lys Val Leu Tyr Leu Leu Ser Gln Leu
                50                  55                  60

Gln Gln Ser Gln Met Thr Glu Lys Gln Leu
                65                  70

<210> SEQ ID NO 8
<211> LENGTH: 75
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 290..364

<400> SEQUENCE: 8

Lys Gln Lys Met Asp Glu Leu His Lys Lys Leu His Gln Val Val
                 5                  10                  15

Glu Thr Ser His Glu Asp Leu Pro Ala Ser Gln Glu Arg Ser Glu
                20                  25                  30

Val Asn Pro Ala Arg Met Gly Pro Ser Val Gly Ser Gln Gln Glu
                35                  40                  45

Leu Arg Ala Pro Cys Leu Pro Val Thr Tyr Gln Arg Thr Pro Val
                50                  55                  60

Asn Met Glu Lys Asn Pro Arg Glu Ala Pro Pro Val Val Pro Pro
                65                  70                  75

<210> SEQ ID NO 9
<211> LENGTH: 76
<212> TYPE: PRT
<213> ORGANISM: Homo sapiens; Eukaryota; Animalia; Metazoa; Chordata;
      Vertebrata;Mammalia;
<220> FEATURE:
<221> NAME/KEY: peptide
<222> LOCATION: 951..1025

<400> SEQUENCE: 9

Glu Glu Ser Val Ser Glu Lys Glu Gln Gln Leu Leu Ser Thr Leu
                 5                  10                  15

Lys Cys Gln Glu Glu Glu Leu Arg Lys Met Gln Glu Val Cys Glu
                20                  25                  30
```

```
Gln Asn Gln Gln Leu Leu Gln Glu Asn Ser Ala Ile Lys Gln Lys
            35                  40                  45

Leu Thr Leu Leu Gln Val Ala Ser Lys Gln Lys Pro His Leu Thr
            50                  55                  60

Arg Asn Ile Phe Gln Ser Pro Asp Ser Ser Phe Glu Tyr Ile Pro
            65                  70                  75

Pro
```